US006020169A

United States Patent [19]
Lee et al.

[11] Patent Number: 6,020,169
[45] Date of Patent: Feb. 1, 2000

[54] PRODUCTION OF SECRETED FOREIGN POLYPEPTIDES IN PLANT CELL CULTURE

[75] Inventors: James M. Lee; Nancy S. Magnuson, both of Pullman, Wash.; Gynheung An, Pohang, Rep. of Korea; Raymond Reeves, Pullman, Wash.

[73] Assignee: Washington State University Research Foundation, Pullman, Wash.

[21] Appl. No.: 08/983,408

[22] PCT Filed: Jul. 19, 1996

[86] PCT No.: PCT/US96/12015

§ 371 Date: Apr. 6, 1998

§ 102(e) Date: Apr. 6, 1998

[87] PCT Pub. No.: WO97/04122

PCT Pub. Date: Feb. 6, 1997

Related U.S. Application Data

[60] Provisional application No. 60/001,269, Jul. 20, 1995.
[51] Int. Cl.[7] .......................... C12N 15/00; C12N 15/29; C12N 15/82
[52] U.S. Cl. ...................... 435/70.1; 435/419; 435/468; 435/69.1; 435/69.8; 536/23.5; 536/23.53; 536/24.1
[58] Field of Search ..................... 435/468, 419, 435/69.1, 69.8, 70.1, 320.1; 536/23.5, 23.53, 24.1

[56] References Cited

U.S. PATENT DOCUMENTS 4,956,282  9/1990  Goodman et al. .

OTHER PUBLICATIONS

Hein et al. Biotechnol. Prog. vol. 7: 455–461, 1991.
Anderson et al. Journal of Applied Polymer Science. vol. 23:2453–2462, 1979.
Hall et al. Proc. Natl. Acad. Sci. USA. vol. 88; 9320–9324, 1991.
Carrington et al. Journal of Virology. vol. 64: 1590–1597, 1990.
Hall Jr. et al., "Nuclear scaffolds and scaffold–attachment regions in higher plants," *Proc. Natl. Acad. Sci. USA*, 88:9320–9324 (1991).
Carrington et al., "CAP–independent enhancement of translation by a plant potyvirus 5' nontranslated region," *Journal of Virology*, 64:1590–1597 (1990).
Hein et al., "Evaluation of immunoglobins from plant cells," *Biotechnol. Prog.*, 7:455–461 (1991).
Anderson et al., "Crosslinking aqueous polyvinyl pyrrolidone solutions by persulfate," *Journal of Applied Polymer Science*, 23:2453–2462 (1979).
Firek et al., "Secretion of a functional single–chain Fv protein in transgenic tobacco plants and cell suspension cultures," *Plant Molecular Biology*, 23:861–870 (1993).
Conrad and Fiedler, "Expression of engineered antibodies in plant cells," *Plant Molecular Biology*, 26:1023–1030 (1994).

De Neve et al., "Assembly of an antibody and its derived antibody fragment in *Nicotiana* and *Arabidopsis*," *Transgenic Research*, 2:227–237 (1993).

Hiatt et al., "Production of antibodies in transgenic plants," *Nature*, 342:76–78 (1989).

Ma et al., "Assembly of monoclonal antibodies with IgG1 and IgA heavy chain domains in transgenic tobacco plants," *Eur. J. Immunol.*, 24:131–138 (1994).

Düring et al., "Synthesis and self–assembly of a functional monoclonal antibody in transgenic *Nicotiana tabacum*," *Plant Molecular Biology*, 15:281–293 (1990).

Benvenuto et al., "Phytoantibodies':a general vector for the expression of immunoglobulin domains in transgenic plants," *Plant Molecular Biology*, 17:865–874 (1991).

Vandekerckhove et al., "Enkephalins produced in transgenic plants using modified 2S seed storage proteins," *Bio/Technology*, 7:929–932 (1989).

Hiatt, "Antibodies produced in plants," *Nature*, 344:469–470 (1990).

Sijmons et al., "Production of correctly processed human serum albumin in transgenic plants," Bio/Technology, 8:217–221 (1990).

Ma et al., "Generation and assembly of secretory antibodies in plants," *Science*, 268:716–719 (1995).

Moffat, "High–Tech Plants Promise a Bumper Crop of New Products," *Science*, 256:770–771 (1992).

Manguson et al., "Enhanced Recovery of a Secreted Mammalian Protein from Suspension Culture of Genetically Modified Tobacco Cells," *Protein Expression and Purification*, 7:220–228 (1996).

*Primary Examiner*—Lynette R. F. Smith
*Assistant Examiner*—Thomas Haas
*Attorney, Agent, or Firm*—Klarquist Sparkman Campbell Leigh & Whinston, LLP

[57] ABSTRACT

Disclosed are methods and compositions for increasing the expression and recovery of heterologous polypeptides secreted by cultured plant cells, including DNA constructs for high-level gene expression, seretion of heterologous polypeptides through both the plasma membrane and cell wall into the plant culture medium to facilitate protein recovery, and novel plant culture media. Recovery of secreted heterologous polypeptides from plant cell culture medium is significantly improved by including in the plant culture medium a polypeptide stabilizer such as polyvinylpyrrolidone.

33 Claims, 13 Drawing Sheets pTL-7SN

PRODUCTION OF SECRETED FOREIGN POLYPEPTIDES IN PLANT CELL CULTURE

This application is a 371 of PCT/US96/12015 filed Jul. 19, 1996, which claims priority to PROVISIONAL APPLICATION NO. 60/001,269, filed on Jul. 20, 1995.

ACKNOWLEDGMENT OF GOVERNMENT SUPPORT

This invention was made with government support under grants nos. BSC-9019522 and BSC-9308407, awarded by the National Science Foundation. The government has certain rights in this invention.

TECHNICAL FIELD

This invention is related to the field of methods and compositions for recombinant production of foreign polypeptides, and more particularly to production of secreted foreign polypeptides in plant cell culture.

BACKGROUND OF THE INVENTION

Transgenic plant cells have been studied over the past several years for potential use in low cost production of high quality, biologically active mammalian proteins (Sijmons et al., *Bio/Technology* 8:217–221, 1990; Vandekerckhove et al., *Bio/Technology* 7:929–932, 1989; Conrad and Fiedler, *Plant Molecular Biology* 26:1023–1030, 1994; and Ma et al., *Science* 268:716–719, 1995). Of the various mammalian proteins studied to date, monoclonal antibodies (MAb) have received the most attention because of their potential value as therapeutic and clinical reagents (reviewed in Conrad and Fiedler, *Plant Molecular Biology* 26:1023–1030, 1994). Initially, individual heavy and light chains were expressed in transgenic tobacco plants, but the expression obtained was exceedingly low (Hiatt et al., *Nature* 342:76–78, 1989). Although it was well known that large macromolecules such as protein multimers do not readily pass through plant cell membranes (Milburn, *Water Flow in Plants*, Longman, London, 1979; Carpita et al., *Science* 205:1144–1147, 1979), two transgenic tobacco plants each expressing either the heavy or light immunoglobulin chains were crossed generating a hybrid plant that coexpressed both chains. The coexpression of both chains led to a large accumulation of antibody within the leaf tissue, an increase from 0.3% to 1.3% of the total leaf protein. Importantly, the antibody retained all its functional and binding capacities. More recently, through successive sexual crosses, it has been possible to generate a functional dimer IgA antibody containing both the J chain and secretory unit (Ma et al., *Science* 268:716–719, 1995). The antibody accumulated at high levels in the protoplastic or apoplastic space in leaf tissue, with antibody accumulation apparently dependent both upon the stabilizing effect of the heavy/light chain dimer formation and on the presence of functional leader sequences, which appeared to be necessary for assembly. Intact functional antibodies can be produced intracellularly in transgenic plants, but intracellular accumulation requires expensive purification of the antibodies from other cellular proteins.

Other studies have demonstrated that functional IgM antibodies could be generated simply by incorporating both heavy and light chain cDNAs into a single construct rather than crossing individual plants possessing the transgene for either the light or heavy chain (During et al., *Plant Mol. Biol.* 15:281–293, 1990). Again, accumulation of the multimeric antibody occurred only intracellularly within the leaf tissue. Nevertheless, the studies did underscore the finding that a leader sequence was necessary for accumulation of the antibody. The source of the leader sequence (mammalian or plant) appeared to play a major role in determining the location of protein accumulation within the cell.

One of the first foreign proteins to be expressed and secreted into the medium from a plant cell was human serum albumin (Sijmons et al., *Bio/Technology* 8:217–221, 1990). The albumin was detected in the culture medium at a level of 0.25 µg/mg of plant protein and appeared to represent the majority of the synthesized albumin suggesting almost all of it was secreted. Unfortunately, because albumin lacks a measurable enzymatic or biological activity, it was not possible to assess the functional capacity of the albumin produced in the plant.

Secretion of functional antibody through the plasma membrane of plant cells has been reported for protoplasts isolated from transgenic plants and for callus cells adapted to suspension culture (Hein et al., *Biotechnol. Prog.* 7:455–561, 1991). However, the levels of secreted antibody detected in both culture systems were extremely low. In other studies, cultured tobacco cells were transformed with a gene encoding a synthetic antibody derivative expressed as a single chain consisting of both the heavy- and light-chain variable domains of the intact immunoglobulin joined together by a flexible peptide linker (Pluckthun, *Immunol. Rev.* 130:151–188, 1991; and Bird et al., *Science* 242:423–426, 1988). This synthetic single-chain antibody retained the full antigen-binding potential of the intact immunoglobulin but accumulated in the extracellular apoplastic space of the transformed cells (Firek et al., *Plant Molecular Biology* 23:861–870, 1993), indicating that the antibody was being transported through the plasma membrane but not through the cell wall to the external environment.

There remains a need for methods and compositions for achieving high level expression and recovery of foreign proteins from plant cells.

SUMMARY OF THE INVENTION

Figure 1:
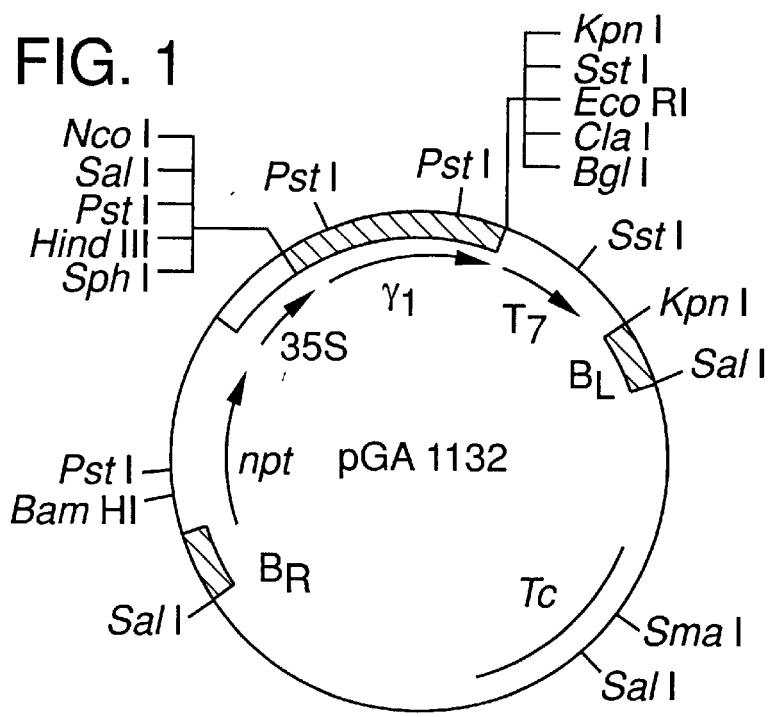
FIG. 1 shows the construction of plasmid pGA1132.

The present invention provides compositions and methods for increasing the expression and recovery of heterologous polypeptides secreted by cultured plant cells.

Methods are provided for the production of a wide variety of heterologous polypeptides, including mammalian polypeptides, in cultured plant cells, preferably in suspension culture. Secretion of the heterologous polypeptides through the plasma membrane and cell wall of the cultured plant cells into the surrounding plant cell culture medium is directed by a signal peptide. Recovery of the secreted polypeptides from plant culture medium is significantly improved by including in the medium a polypeptide stabilizer, which can be non-proteinaceous, e.g., polyvinylpyrrolidone (PVP) and its derivatives, or proteinaceous, e.g., gelatin or serum albumin.

Also encompassed by the present invention are plant culture media that include an amount of a polypeptide stabilizing agent that is effective to increase recovery of a polypeptide secreted into the medium by a plant cell cultured in the medium by at least about 20 percent compared to a control medium lacking the polypeptide stabilizing agent.

Also encompassed by the present invention are DNA constructs for high level expression and secretion of heterologous polypeptides in plant cells. Such DNA constructs include: a promoter that is functional in a given host plant cell; operably linked to the promoter, a sequence coding for a fusion polypeptide that includes a signal peptide for directing secretion of a polypeptide through the plasma membrane and cell wall of a plant cell and a polypeptide of interest, e.g., a mammalian polypeptide; and a potyvirus (e.g., tobacco etch virus) 5'-leader sequence and/or a nuclear scaffold attachment region (SAR) sequence.

Detailed Description of the Invention

Plant suspension culture systems provide significant advantages over protein production in intact transgenic plants, which requires cultivation, harvesting and expensive extraction procedures to obtain non-secreted foreign proteins. Plant cell culture provides distinct advantages over other expression systems in terms of the purification of foreign polypeptides. Plant cells can be grown on an inexpensive defined medium lacking any polypeptide or other material that would complicate the purification of the secreted polypeptide or interfere with its biological activity. Moreover, the cultured plant cells appear to secrete few proteins into the culture medium. Also, high levels of contamination by proteins and other substances (e.g., endotoxin in the case of expression in E. coli) encountered in other expression systems, e.g., in the purification of polypeptides produced intracellularly after disrupting cells to release the polypeptide, are avoided. It also appears that proteolysis of secreted polypeptides in the plant cell culture medium is limited, at least in the presence of PVP or another protein stabilizing agent. Finally, protein glycosylation and processing in plant cells is similar to that of mammalian cells.

The present invention provides methods and compositions for the economic production in plant cells of large quantities of foreign polypeptides, such as clinically or therapeutically useful proteins, in a biologically active form. It has been found that signal peptides from mammalian polypeptides (e.g., antibody heavy chains and interleukins) can direct the secretion of foreign polypeptides not only through the plasma membrane (and thus into the apoplastic space) but also through the plant cell wall and into the surrounding plant culture medium. In order to maximize the yield of a foreign polypeptide expressed in a plant cell culture system, it is preferable to ensure high level expression of the polypeptide-encoding transgene through the use of such sequences as the tobacco etch viral (TEV) 5'-leader sequence and a nuclear scaffold attachment region (SAR) sequence (or matrix attachment region, MAR) flanking the expressed transgene, for example. It has also been discovered that including a protein stabilizing agent in a plant culture medium can dramatically increase the recovery of foreign proteins secreted from plant cells cultured in such a medium.

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

Secretion

"Secretion"

As the term is used herein, secretion means secretion of a polypeptide across both the plasma membrane and the cell wall of a host plant cell. It should be noted that, in the scientific literature related to the production of foreign polypeptides in plant cell systems, the term "secretion" often is used to indicated secretion into the apoplastic space, i.e., secretion across the plasma membrane but not across the cell wall.

Heterologous Polypeptides

A "heterologous" or "foreign" polypeptide is a polypeptide encoded by a nucleic acid not normally present in a particular plant host cell used for production of the polypeptide. The compositions and methods of the present invention are useful for the production of a wide variety of heterologous polypeptides, including mammalian polypeptides. Examples of polypeptides that can be expressed, secreted, and recovered from plant cells according to the present invention include, but are not limited to: immunoglobulins; cytokines; hormones (e.g., granulocyte-monocyte colony stimulating factor, insulin, prolactin, etc.); growth factors (e.g., epidermal growth factor, platelet-derived growth factor, nerve growth factor, etc.); blood clotting factors; complement components; fibrinolytic polypeptides; polymerases; and enzymes involved in metabolism of, for example, lipids, amino acids, sugars, nucleic acids, polysaccharides (e.g., adenosine deaminase, hypoxanthine guanine ribosyl transferase).

Signal Peptide

The nature of the signal peptide or leader sequence appears to be crucial for the successful secretion of foreign proteins from plant cells into the culture medium (Chrispeels, *Annu. Rev. Plant Physiol. Plant Mol. Biol.* 42:21–53, 1991.) Secreted proteins are generally translated as precursor polypeptides that include a "signal sequence" or "signal peptide," generally located at the amino-terminus of the precursor polypeptide, that is recognized by and interacts with a receptor protein on the membrane of the endoplasmic reticulum (ER) to direct the transfer of the growing polypeptide chain across the membrane and into the endoplasmic reticulum for eventual secretion from the cell. The signal peptide is commonly cleaved from the precursor polypeptide to produce a "mature" polypeptide lacking the signal peptide. A signal peptide from a secreted protein native to the cultured host plant cell (i.e., a "native" signal peptide) or a signal peptide from a secreted polypeptide from another species, whether a plant species or a mammalian or other eukaryotic species (i.e., a "heterologous" signal peptide) can be used to target foreign polypeptides for secretion from plant cells when fused to the foreign polypeptide by conventional recombinant DNA techniques.

The Examples below demonstrate that foreign polypeptides expressed in plant cell suspension culture can be efficiently secreted through the plasma membrane and cell wall of a host plant cell into the extracellular medium. Either signal peptides of plant origin (e.g., the N-terminal signal peptide from the tobacco PR1a protein, Firek et al., *Plant Molecular Biology* 23:861–870, 1993) or signal peptides from foreign eukaryotic secreted polypeptides, e.g., mammalian signal peptides, can be employed to achieve secretion of foreign polypeptides from plant host cells. For example, as discussed in detail in the Example below, secretion of the mouse antibody heavy chain γ and interleukin (IL)-2, 4, and 10 polypeptides from *Nicotiana tabacum* NT-1 suspension cultures was directed by the N-terminal signal peptides associated with each of these mammalian polypeptides.

Size of the Secreted Foreign Polypeptide

It was previously estimated that the exclusion limit of the plant cell wall is equivalent to a globular protein of approximately 20–29 kDa (Carpita et al., *Science* 205:1144–1147, 1979; Pluckthum, *Immunol. Rev.* 130:151–188, 1991; and Bird et al., *Science* 242:423–426, 1988). The results reported herein indicate that polypeptide chains with molecular masses of at least about ~50 kDa are capable of passing through the cell wall into the medium.

Plant Culture Media

Any conventional plant culture medium can be used in the practice of the present invention, including, but not limited to, the following well known media: Anderson (Anderson, In Vitro 14:334, 1978; Anderson, *Act. Hort.*, 112:13, 1980), Chee and Pool (*Sci. Hort.* 32:85, 1987), CLC/Ipomoea (CP) (Chee et al., *J. Am. Soc. Hort. Sci.* 117:663, 1992), Chu ($N_6$) (Chu et al., *Scientia Sinic.* 18:659, 1975; Chu, *Proc. Symp. Plant Tiss. Cult.*, Peking 43, 1978), DCR (Gupta and Durzan, *Plant Cell Rep.* 4:177, 1985), DKW/Juglans (Driver and Kuniyuki, *HortScience* 19:507, 1984; McGranahan et al., in: Bonga and Durzan, eds., *Cell and Tissue Culture in Forestry*, Martinus Nijhoff, Dordrecht, 1987), De Greef and Jacobs (De Greef and Jacobs, *Plant Sci. Lett.* 17:55, 1979), Eriksson (ER) (Eriksson, *Physiol. Plant.* 18:976, 1965), Gamborg's B-5 (Gamborg et al., *Exp. Cell Res.* 50:151, 1968), Gresshoff and Doy (DBM2) (Gresshoff and Doy, Z *Pflanzenphysiol.* 73:132, 1974), Heller's (Heller, *Ann. Sci. Nat. Bot. Biol. Veg.* 11th Ser. 14:1, 1953), Hoagland's (Hoagland and Arnon, *Circular* 347, Calif. Agr. Exp. Stat., Berkeley, 1950), Kao and Michayluk (Kao and Michayluk, *Planta* 126:105, 1975), Linsmaier and Skoog (Linsmaier and Skoog, *Physiol. Plant.* 18:100, 1965), Litvay's (LM) (Litvay et al., *Plant Cell Rep.* 4:325, 1985), McCown's Woody Plant medium (Lloyd and McCown, *Proc. Int. Plant Prop. Soc.* 30:421, 1981), Murashige and Skoog and various well-known modifications thereof (Murashige and Skoog, *Physiol. Plant.* 15:473, 1962), Nitsch and Nitsch (Nitsch and Nitsch, *Science* 163:85, 1969), Quoirin and Lepoivre (Quoirin et al., C. R. *Res. Sta. Cult. Fruit Mar.*, Gembloux 93, 1977), Schenk and Hildebrandt (Schenk and Hildebrandt, *Can. J. Bot.* 50:199, 1972), White's (White, *The Cultivation of Animal and Plant Cells*, Ronald Press, NY, 1963), etc. A number of such plant culture media are commercially available from Sigma (St. Louis, Mo.) and other vendors as dry (powdered) media and dry basal salts mixtures, for example. The term "plant culture medium"

thus includes both aqueous media and dry and concentrated media to which water can be added to produce aqueous media for culturing plant cells.

To enhance recovery of proteins secreted from plant cells grown in such a medium, it is preferred that an effective amount protein stabilizing agent be added to the media. To that end, one embodiment of the present invention is a plant culture medium (dried, concentrated, or diluted to a concentration useful for plant cell culture) including an "effective amount" of such a protein stabilizing agent.

Protein Stabilizing Agents

Recovery of secreted polypeptides can be dramatically improved by including an appropriate protein stabilizing agent in the plant cell growth medium. A number of substances such as PVP have been employed during protein purification from lysed bacterial, mammalian, plant and other cells to prevent protein denaturation and the loss of biological activity (see, e.g., Sijmons et al., *Bio/Technology* 8:217–221, 1990). However, such agents have not been added directly to plant culture media to enhance the recovery of polypeptides secreted by plant cells cultured in such media.

In general, protein stabilizing agents can include any substance conventionally employed during purification of a particular polypeptide to maintain protein concentration and activity, e.g., by preventing protein degradation and denaturation. A protein stabilizing agent according to the present invention should be non-phytotoxic at the concentrations employed and preferably does not interfere with purification of the secreted foreign polypeptide. In addition, the protein stabilizing agent is preferably used at levels that do not substantially reduce plant cell viability and integrity, protein expression, and growth and cell division. For this reason, for example, reducing agents such as β-mercaptoethanol or dithiothreitol, which would be harsh on plant cells in culture, should be avoided except, perhaps, at low concentrations. It is also preferable that the protein stabilizing agent not support or encourage bacterial growth in the culture medium.

Protein stabilizing agents useful for the practice of the invention can include, but are not limited to: non-proteinaceous protein stabilizing agents such as polyvinylpyrrolidone (PVP) and derivatives thereof, carbohydrates (e.g., saccharides and polysaccharides such as maltose, sucrose, dextran, etc.), polyols (e.g., glycerol), dimethylsulfoxide (DMSO), and detergents (e.g., CHAPS, CHAPSO, zwittergens such as zwittergens 310 and 312, octoglucoside, etc.); and proteinaceous protein stabilizing agents, such as gelatin or bovine serum albumin).

The mechanism by which such protein stabilizing agents act to enhance protein recovery is not known, although it is possible that they block nonspecific interactions between the secreted polypeptide and the glass or plastic walls of the culture vessel (or, perhaps, the plant cells themselves).

An "effective amount" of a protein stabilizing agent is an amount, when added to a given volume of a plant culture medium, that significantly increases recovery of a secreted polypeptide from the medium, i.e., to increase protein recovery by a statistically significant amount. Preferably, recovery is increased by at least 20%, more preferably 50%, most preferably 100%, as compared with control medium that is otherwise identical except that it lacks the protein stabilizing agent. The protein stabilizing agent is preferably present in the plant culture medium at a concentration of about 0.1 g/l to about 100.0 g/l (about 0.01% to about 10%). The concentration of the protein stabilizing agent will preferably not exceed levels at which maximum recovery of the secreted polypeptide is observed.

Figure 16A:
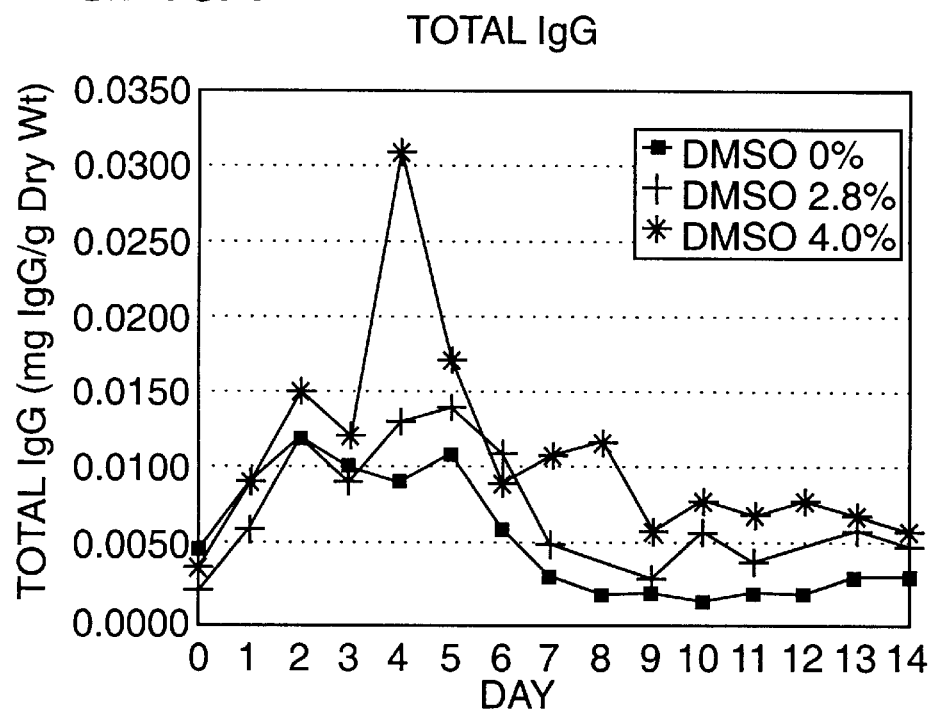
FIG. 16 shows the effect of varying concentrations of 0%, 2.8%, and 4.0% dimethylsulfoxide (DMSO) on total IgG (A) and extracellular IgG (B) produced by suspension cultures of a tobacco suspension culture.
Figure 16B:
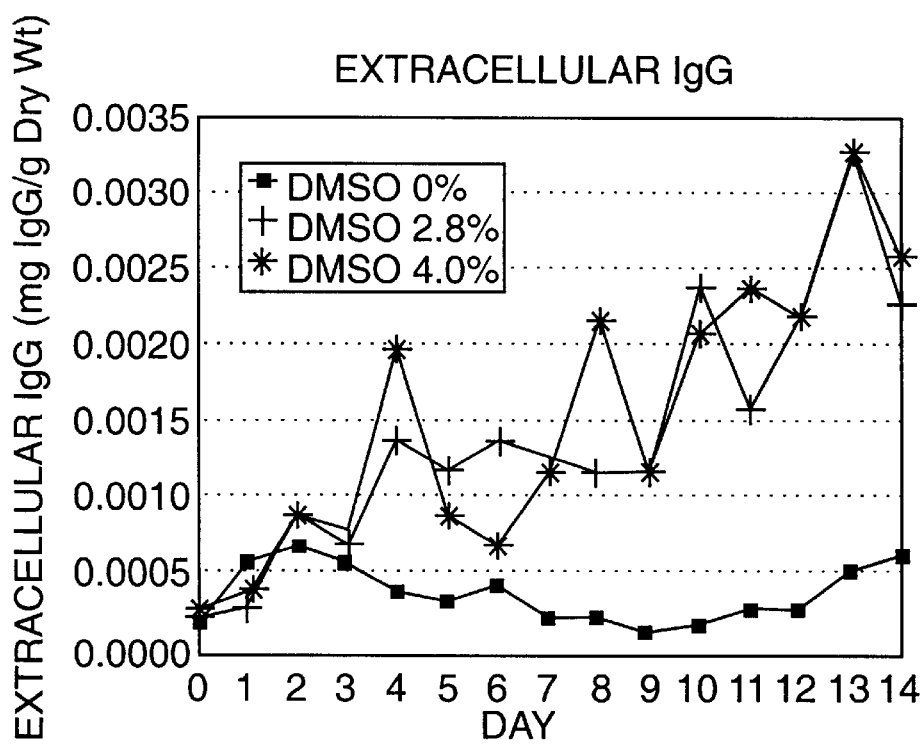

For example, the presence of 0.75 g/l (0.075%) polyvinylpyrrolidone (PVP) in a plant culture medium resulted in a 35-fold increase in the yield of an antibody heavy chain compared to control medium lacking PVP. PVP concentrations ranging from 0.25 g/l to 3.0 g/l were tested and all concentrations significantly increased recovery of a secreted antibody heavy chain protein, with optimal protein recovery at about 0.75 g/l. Gelatin has been tested at 0, 1, 5, 10, and 15 g/l, and optimal protein recovery was observed at about 5 g/l (0.5%) (5 g/l was more effective than 1 g/l in enhancing MAb HC recovery from plant culture media, but 5 g/l was as effective as 10 or 15 g/l). DMSO has been tested at 0%, 2.8% and 4.0%. Both 2.8% and 4.0% DMSO significantly improved recovery of MAb HC from plant culture media (FIG. 16). Protein recovery was approximately the same using either 2.8% or 4.0% DMSO.

Plant Transformation and Cell Culture

The present invention can be practiced with any plant variety for which cells of the plant can be transformed with an DNA construct suitable for expression of a foreign polypeptide and cultured under standard plant cell culture conditions. Suspension culture is preferred, although callus culture or other conventional plant cell culture methods may be used.

Nucleic acids can be expressed in plants or plant cells under the control of a suitable operably linked promoter that is capable of expression in a given plant cell. Any conventional method can be employed for plant cell transformation, culture, and regeneration, including, but not limited to, those described in the Examples below.

Conventional methods for introduction of foreign DNA into plant cells include, but are not limited to: (1) Agrobacterium-mediated transformation (Lichtenstein and Fuller In: *Genetic Engineering*, Vol 6, Rigby, ed., London, Academic Press, 1987; and Lichtenstein and Draper, in: *DNA Cloning*, Vol II, Glover, ed., Oxford, IRI Press, 1985); (2) particle delivery (see, e.g., Gordon-Kamm et al., *Plant Cell* 2:603, 1990; or BioRad Technical Bulletin 1687), (3) microinjection (see, e.g., Green et al., *Plant Tissue and Cell Culture*, Academic Press, New York, 1987), (4) polyethylene glycol (PEG) procedures (see, e.g., Draper et al., *Plant Cell Physiol.* 23:451, 1982); Zhang and Wu, *Theor. Appl. Genet.* 76:835, 1988), (5) liposome-mediated DNA uptake (see, e.g., Freeman et al., *Plant Cell Physiol.* 25:1353, 1984), (6) electroporation (see, e.g., Fromm et al., *Nature* 319:791, 1986); and (7) the vortexing method (see, e.g., Kindle, *Proc. Natl. Acad. Sci. USA* 87:1228, 1990).

The term "plant" encompasses any higher plant and progeny thereof, including monocots (e.g., rice), dicots (e.g., tobacco, Arabidopsis, carrot, etc.), gymnosperms, etc. The plant cell expression system disclosed in the Examples below, which employs *Nicotiana tabacum* NT-1 expression culture cells, is characterized by rapid cell growth and stable foreign protein expression during long-term subculturing (>4 years).

Nucleic Acids

"Isolated"

An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid-purification methods. The term also embraces nucleic acids prepared by recombinant expression in a host cell as well as chemically synthesized nucleic acids.

Operably Linked

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant"

A "recombinant" nucleic acid is one that has a sequence that is not naturally occurring or has a sequence that is made by an artificial combination of two otherwise saparated segments of sequence. This artificial combination is often accomplished by chemical synthesis or, more commonly, by the artificial manipulation of isolated segments of nucleic acids, e.g., by genetic engineering techniques.

Techniques for nucleic-acid manipulation are described generally in, for example, *Molecular Cloning: A Laboratory Manual,* 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications,* Academic Press: San Diego, 1990.

Vectors, Transformation, Host Cells

Recombinant nucleic-acid constructs are employed in the practice of the present invention, typically DNA constructs, or "vectors," that are capable of introduction into and replication and expression in a plant cell. The DNA constructs may also replicate in a unicellular host, such as *E. coli* or other commonly used bacteria or in a yeast, mammalian, plant or other eukaryotic cell. Preferably, such a nucleic-acid construct is a vector comprising a replication system recognized by the host plant cell. For the practice of the present invention, conventional compositions and techniques for preparing and using vectors, host cells, introduction of vectors into host cells, etc., are employed.

A cell, tissue, organ, or organism into which has been introduced a foreign nucleic acid, such as a recombinant vector, is considered "transformed" or "transgenic." The DNA construct that is present in a transgenic host cell, particularly a transgenic plant, is referred to as a "transgene." The term "transgenic" or "transformed" when referring to a cell or organism, also includes (1) progeny of the cell or organism and (2) plants produced from a breeding program employing such a "transgenic" plant as a parent in a cross and exhibiting an altered phenotype resulting from the presence of the recombinant DNA construct.

A number of vectors suitable for expression of polypeptides in plant cells have been described in, e.g., Pouwels et al., *Cloning Vectors: A Laboratory Manual,* 1985, supp. 1987); Weissbach and Weissbach, *Methods for Plant Molecular Biology,* Academic Press, 1989; and Gelvin et al., *Plant Molecular Biology Manual,* Kluwer Academic Publishers, 1990. Typically, plant expression vectors include, for example, one or more cloned plant genes under the transcriptional control of a promoter sequence that is functional in a given host plant cell, additional 5' and 3' regulatory sequences, and a marker, preferably a dominant selectable marker. Such plant expression vectors also can contain a promoter (e.g., a regulatory region controlling inducible or constitutive, environmentally-or developmentally-regulated, or cell- or tissue-specific expression), a transcription initiation start site, and a ribosome binding site. In addition, plant expression vectors optionally include, for example: RNA processing signals, e.g., introns, which may be positioned upstream or downstream of a polypeptide-encoding sequence in the transgene; regulatory sequences from the 3'-untranslated region of plant genes (Thornburg et al., *Proc. Natl. Acad. Sci. USA* 84:744 (1987); An et al., *Plant Cell* 1:115 (1989), e.g., a 3' terminator region to increase mRNA stability of the mRNA, such as the PI-II terminator region of potato or the octopine or nopaline synthase 3' terminator regions; and a polyadenylation signal. In order to increase expression of the expression of the heterologous transgene expression, it is preferable to also include a 5' leader sequence, e.g., the tobacco etch viral (TEV) 5'-leader sequence (Gallie et al., *Gene* 165:233–238, 1995) and of the presence of plant nuclear scaffold or matrix attachment region sequences flanking the heterologous transgene, e.g., the tobacco SAR/MAR (Allen et al., *Plant Cell* 8:899–913, 1996; Hall et al., *Proc. Natl. Acad. USA* 88:9320–9324, 1991).

Examples of constitutive plant promoters useful for expressing heterologous polypeptides in plant cells include, but are not limited to, the cauliflower mosaic virus (CaMV) 35S promoter, which confers constitutive, high-level expression in most plant tissues (see, e.g., Odel et al., *Nature* 313:810, 1985), including monocots (see, e.g., Dekeyser et al., *Plant Cell* 2:591, 1990; Terada and Shimamoto, *Mol. Gen. Genet.* 220:389, 1990); the nopaline synthase promoter (An et al., *Plant Physiol.* 88:547, 1988), and the octopine synthase promoter (Fromm et al., *Plant Cell* 1:977, 1989).

A variety of plant gene promoters that are regulated in response to environmental, hormonal, chemical, and/or developmental signals, also can be used for expression of foreign polypeptides in plant cells, including promoters regulated by (1) heat (Callis et al., *Plant Physiol.* 88:965, 1988), (2) light (e.g., pea rbcS-3A promoter, Kuhlemeier et al., *Plant Cell* 1:471, 1989; maize rbcs promoter, Schaffner and Sheen, *Plant Cell* 3:997, 1991; or chlorophyll a/b-binding protein promoter, Simpson et al., *EMBO J.* 4:2723, 1985), (3) hormones, such as abscisic acid (Marcotte et al., *Plant Cell* 1:969, 1989), (4) wounding (e.g., wunI, Siebertz et al., *Plant Cell* 1:961, 1989); or (5) chemicals such as methyl jasminate, salicylic acid, or Safener. It may also be advantageous to employ (6) organ-specific promoters (e. g., Roshal et al., *EMBO J.* 6:1155, 1987; Schernthaner et al., *EMBO J.* 7:1249, 1988; Bustos et al., *Plant Cell* 1:839, 1989).

Useful dominant selectable marker genes include genes encoding antibiotic resistance genes (e.g., resistance to hygromycin, kanamycin, bleomycin, G418, streptomycin, or spectinomycin); and herbicide resistance genes (e.g., phosphinothricin acetyltransferase). A useful strategy for selection of transformants for herbicide resistance is described, e.g., in Vasil, *Cell Culture and Somatic Cell Genetics of Plants,* Vols. I–III, Laboratory Procedures and Their Applications Academic Press, New York, 1984.

Polypeptides

The present invention involves the production of foreign polypeptides by recombinant means in a plant cell, e.g., in a suspension culture.

"Isolated," "Purified," "Homogeneous" Polypeptides

A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolated. A monomeric polypeptide is isolated when at least 60% by weight of a sample is composed of the polypeptide, preferably at least 80%, more preferably at least 95%, and most preferably at least 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional method.

Protein Purification

Polypeptides can be purified by any of the means known in the art. Various methods of protein purification are described, e.g., in *Guide to Protein Purification,* ed. Deutscher, *Meth. Enzymol* 185, Academic Press, San Diego, 1990; and Scopes, *Protein Purification: Principles and Practice,* Springer Verlag, New York, 1982.

Fusion Polypeptides

A fusion polypeptide is one comprising amino acid sequences derived from two different polypeptides. Such fusion polypeptides can thus exhibit biological properties, including, but not limited to, signal peptides or antigenic determinants, derived from each of the fused sequences. Such fusion polypeptides can be produced, for example by joining all or part of two (or more) different protein-coding DNA sequences by conventional recombinant means and placing them under the control of a single promoter, signal peptide, etc.

DNA encoding a fusion polypeptide can be constructed, for example, by joining DNA encoding a signal peptide of a first polypeptide to the amino terminus of a protein-coding region of DNA sequence encoding a second polypeptide (e.g., a polypeptide lacking a signal peptide), in order to cause the secretion of the second polypeptide from a transformed plant cell (generally after the signal peptide is cleaved to produce a "mature" second polypeptide lacking the signal peptide). In order to make protein purification easier or more efficient, e.g., one can join DNA encoding a polypeptide of interest to a DNA sequence encoding a polypeptide that is easily purified, e.g., by affinity chromatography, including, but not limited to, an antibody or binding fragment thereof or an antigen recognized thereby; a ligand or receptor therefor; or other affinity pairs known in the art, including, for example "polyhistidine tags" (for purification on a nickel column), glutathione transferase (for purification on a glutathione-Sepharose column), etc.

The fusion partner can be joined to a polypeptide of interest by a peptide linker to allow proper folding of the antibody portion of the fusion protein to form an antigen binding site. Peptide linkers between fusion partners can also be used to introduce convenient sites for proteolysis to allow a the fusion protein to be cleaved and a protein of interest to be purified away from its fusion partner.

Preferably, the total size of the fusion polypeptide is approximately 50 kDa or less.

Antibodies

For the preparation and use of antibodies, including various immunopurification and immunoassay techniques and applications, see, e.g., Goding, *Monoclonal Antibodies: Principles and Practice,* 2d ed, Academic Press, New York, 1986; and Harlow and Lane, *Antibodies: A Laboratory Manual,* Cold Spring Harbor Laboratory, Cold Spring Harbor, N.Y., 1988.

The invention will be better understood by reference to the following Examples, which are intended to merely illustrate the best mode now known for practicing the invention. The scope of the invention is not to be considered limited thereto, however.

EXAMPLES

Example 1

Secretion of a Mouse Immunoglobulin γ Heavy Chain (Mab HC) from *Nicotiana tabacum* Cells in Suspension Culture Materials and Methods Construction of Vector The entire cDNA sequence of the murine monoclonal antibody heavy chain (MAb HC) gene specific for p-azophenylarsonate (plasmid pH$\gamma_1$360E, [Hasemann et al., *Proc. Natl. Acad. Sci. USA* 87:3942–3946, 1990]) was inserted into plasmid pGA648 at Nco I and Kpn I sites to form plasmid pGA1130. Plasmid pGA648 was derived from pUC19 by converting the Xba I site to a Nco I site.

The 1.75 kb MAb HC cDNA was excised as an Eco RI-Hind III fragment from pGA1130 and subsequently introduced into a binary vector pGA748 (Chung et al., *Plant Mol. Biol.* 26:657–665, 1994), a derivative of pGA643 (An et al., "Binary Vectors," In: Gelvin and Schilperoort, eds., *Plant Molecular Biology Manual,* Kluwer Academic, Dordrecht, Belgium, 1988, pp. A3/1–19) to form plasmid pGA1132 (FIG. 1). The MAb HC cDNA (γ1) is located downstream of CaMV 35S promoter (–419 to +1) (Odell et al., *Nature* 313:810–812, 1985) and terminated by the T-DNA transcript 7 gene terminator. Plasmid PGA1132 carries a kanamycin resistant gene (npt) and a tetracycline resistant gene (Tc). BL and BR are the left and the right border of a T-DNA.

Genetically Modified Plant Cells

The plasmid PGA1132 was transferred by the freeze-thaw method (An et al., *Plant Molecular Biology Manual* A3: 1–19, 1988) into *Agrobacaertum tumefaciens* LBA4404 that carried pAL4404 as a helper Ti plasmid (Hoekema et al., *Nature* 303:179–180, 1983).

*Nicotiana tabacum*-clone 1 (NT-1) suspension cells were co-cultivated for three days with *Agrobacterium tumaciens* carrying a binary Ti plasmid vector (An et al., *Plant Molecular Biology Manual* A3:1–19, 1988). The genetically modified cells were plated onto Murashige and Skoog (MS) agar medium containing 50 μg/ml kanamycin for the selection of transformants (An et al., *Plant Molecular Biology Manual* A3:1–19, 1988). Suspension cultures were developed by sub-culturing the transformed callus in a liquid medium containing 4.3 mg/ml MS salt supplemented with 3% sucrose, 0.18 mg/ml $KH_2PO_4$, 0.1 mg/ml inositol, 1 μg/ml thiamine hydrochloride, 0.2 μg/ml 2,4-dichlorophenoxyacetic acid (2,4-D), 100 μg/ml cefotaxime and 50 μg/ml kanamycin. The genetically modified cells were cultivated in 250-ml Erlenmeyer flasks (working volume: 60 ml) at 29° C. agitated at 150 rpm on an orbital shaker. The suspension cell lines were sub-cultured weekly with a 5% inoculum of seven-day old cells.

Northern Blot Analysis

Total RNA was isolated from exponentially growing plant suspension culture (four days after subculture) by the guanidinium thiocyanate-CsCl purification procedures (Sambrook et al., *Molecular cloning: A Laboratory Manual,* 2nd ed., Cold Spring Harbor Laboratory Press, 1989). The RNA samples (50 μg) were fractionated by electrophoresis in a 1.3% formaldehyde-agarose gel and capillary-blotted onto Zeta-Probe nylon membrane (Bio-Rad Laboratories, Richmond, Calif.). The RNA blots were hybridized with a 1.75 kb DNA fragment containing the MAb HC cDNA that was labeled with α³²P-dCTP and T7 DNA polymerase (Pharmacia LKB Biotechnology, Piscataway, N.J.). The molecular weight marker was a 0.24–9.5 kb RNA ladder (Bethesda Research Laboratories, Gaithersburg, Md.).

Protein Extraction and Analysis

Cell culture suspensions were centrifuged and the supernatant saved for the assays of the extracellular MAb HC. Two grams of cell pellets were resspended in 10 ml high salt buffer (pH 7.5) consisting of 50 mM Tris-HCl, 0.5 M NaCl, 0.05% Nonidet P-40, 0.18 mg/ml phenylmethyl sulfonylfluoride, and 15 μg/ml leupeptin. While kept at 4° C., the suspension was sonicated four times with eight-second bursts and then centrifuged at 15,000×g for 5 minutes. The supernatant was saved for the analysis of intracellular protein composition. For analysis of protein composition, 1.0 ml aliquots of this supernatant was precipitated with trichloroacetic acid (TCA, 15% final concentration) at 4° C. for 30 minutes and then microfuged for 20 minutes at 4° C. The protein pellets were washed three times with ice-cold acetone and dried in a speed vac. The pellets were then dissolved in 100 mM Tris, pH 8.0 and normalized for protein concentration. Protein concentration was measured using the Bradford reagent (Bio-Rad laboratories, Richmond, Calif.).

The level of MAb HC production was measured by an enzyme-linked immunosorbent assay (ELISA) using affinity purified goat antibody to mouse IgG (Organon Teknika Co., Durham, N.C.), alkaline phosphatase-labeled goat anti-mouse IgG heavy-chain-specific (Southern Biotechnology Associates, Inc., Birmingham, Ala.), and p-nitrophenyl phosphate (Sigma, St. Louis, Mo.).

Analysis for Antibody Activity

The MAb HC derived either from culture medium or from cell lysates was tested for antibody activity by the ability to bind to specific antigen and to protein G (a measure of heavy-chain constant region activity). One-milliliter aliquots of culture medium from six-day-old cultures were incubated with either 20 μL of protein G agarose (Boehringer Mannheim) or p-azophenylarsonate-coupled lysine-sepharose 4-B beads (Williams and Chase, *Methods Immunol. Immunochem.* 1:120, 1967). The samples were gently mixed for 2 hours at 10° C. Following incubation, the beads were washed three times with 1 ml of phosphate-buffered saline (PBS) made 0.05% in Tween-20. After the last wash, the beads were resuspended in 20 μL PBS and 10 μL of 6× sample buffer added to each sample. The samples were subsequently analyzed by sodium dodecyl sulfate-polyacrylamide gel electrophoresis (SDS-PAGE) as described (Laemmli, *Nature (Lond.)* 227:680–683, 1970). Western blot analysis was carried out as described (Coligan et al., *Current Protocols in Immunology,* John Wiley & Sons, N.Y., 1990) with goat anti-mouse IgG-biotin (γ chain specific; Southern Biotechnology Associates, Inc.) used at 1:2000 as the primary antibody and avidin conjugated-peroxidase (Sigma) used at 1:20,000 as the secondary reagent. The immune complexes were detected with Enhanced Chemiluminesence™ (Amersham). The authentic mouse Ig γ heavy chain with anti-p-azophenylarsonate specificity, produced in Sf9 insect cells using the baculovirus expression system (Hasemann et al., *Proc. Natl. Acad. Sci. USA* 87:3942–3946, 1990), was used as a control for post-translational modification and activity.

Results

Generation of Transgenic Tobacco Cells

Eighty-six independently transformed tobacco calli were selected in the presence of kanamycin and maintained on agar medium. Seventy-six percent of the cell lines were positive in ELISA for MAb HC. Seven of the 76 transformed calli were selected and developed into suspension cultures. Six of these cell lines (No. 35, 41, 47, 49, 64, and 70) produced MAb HC whereas in one of the cell lines (No. 27), the MAb HC was undetectable. Table 1 shows averaged results from four serial batch culture experiments to determine the relative concentrations of total MAb HC produced after growth in suspension culture for four days. In these experiments, concentration of MAb HC were measured by ELISA in terms of μg MAb HC/g cell (DC) to facilitate comparison of MAb HC production in intact calli. The control used was an untransformed NT-1 cell line. It was found that yields of MAb HC from cells in suspension culture were similar to those obtained from the lysates of whole calli. Becaouse clone No. 70 produced the highest concentration of MAb HC (14.2 μg/g dry weight), it was chosen for further study.

TABLE 1

MAb HC protein yields in four-day-old suspension cultures of seven different clones

| Clone Number | MAb HC (μg/g DC) |
|---|---|
| Control (untransformed NT-1) | 0 |
| 27 | 0 |
| 35 | 4.6 ± 1.3 |
| 41 | 3.7 ± 2.2 |
| 47 | 3.6 ± 1.5 |
| 49 | 1.6 ± 0.5 |
| 64 | 3.1 ± 1.3 |
| 70 | 14.2 ± 4.1 |

Northern Blot Analysis

To determine if MAb HC production correlated with the expression of mRNA level, total RNA was isolated from four-day-old suspension cultures and the steady-state level of the MAb HC transcript measured by Northern blot analysis. An equal amount of total RNA (50 μg) was loaded in each lane of the gel as determined by ethidium bromide staining of the 18S and 28S ribosomal RNAs in each sample.

Figure 2:
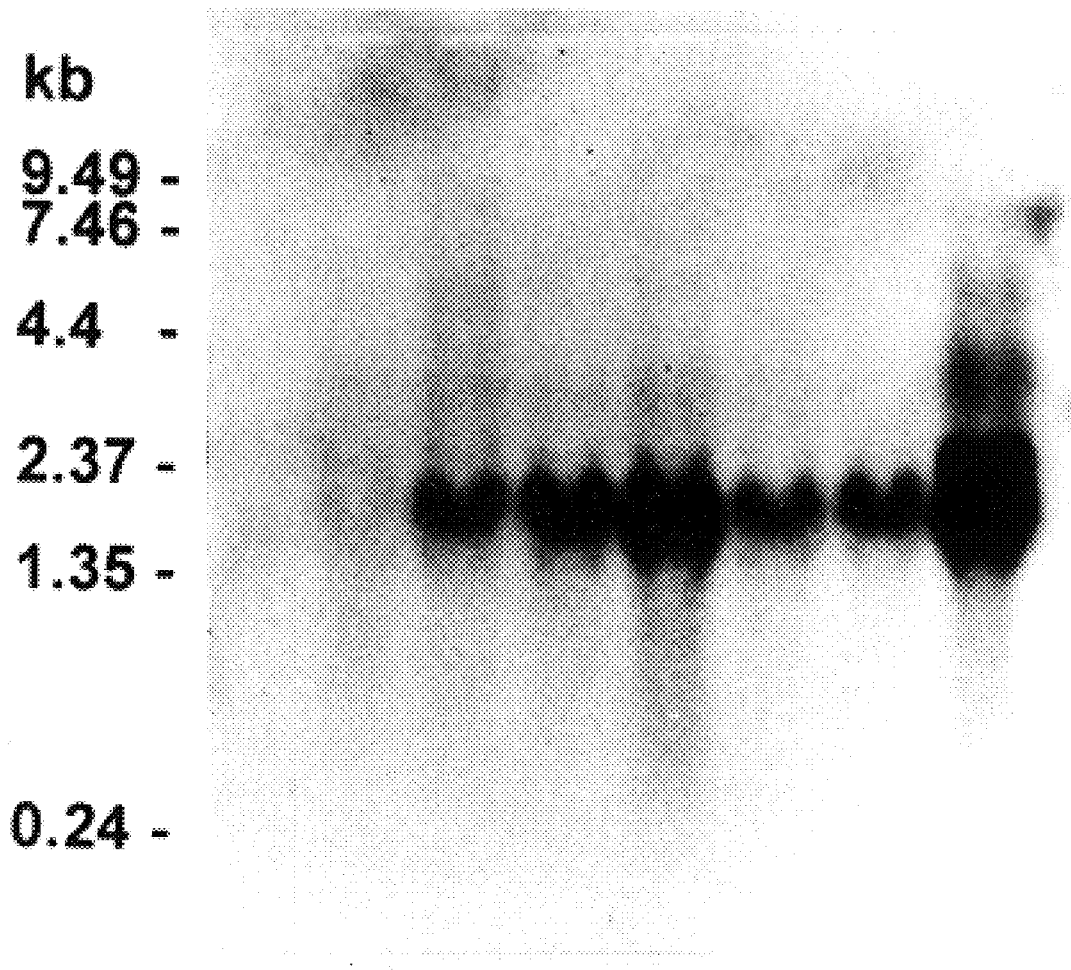
FIG. 2 shows the results of Northern blot analysis of MAb HC mRNA from genetically engineered tobacco cells. Lane NT1, RNA extracted from 4-day old untransformed tobacco cells. Lanes 27, 35, 41, 47, 49, 64, and 70, RNA extracted from four-day old transformed tobacco cells.

FIG. 2 shows the results of the Northern blot analysis. All transformed cell lines expressed the antibody mRNA except clone 27. This was consistent with the ELISA analysis which also indicated clone 27 was negative for MAb HC production. Antibody yields determined by ELISA were nearly always proportional to mRNA expression levels. The major hybridizing band in transgenic cells was approximately 2.2 kb which is the expected transcript size for the MAb HC. The higher molecular weight bands present in the transformed cell lines are thought to be due to unprocessed MAb HC mRNAs often found in plant cells. As observed for the MAb HC protein, the level of the mRNA varied significantly among the transformants.

Batch Suspension Cultures of Transgenic Plant Cells

Figure 3:
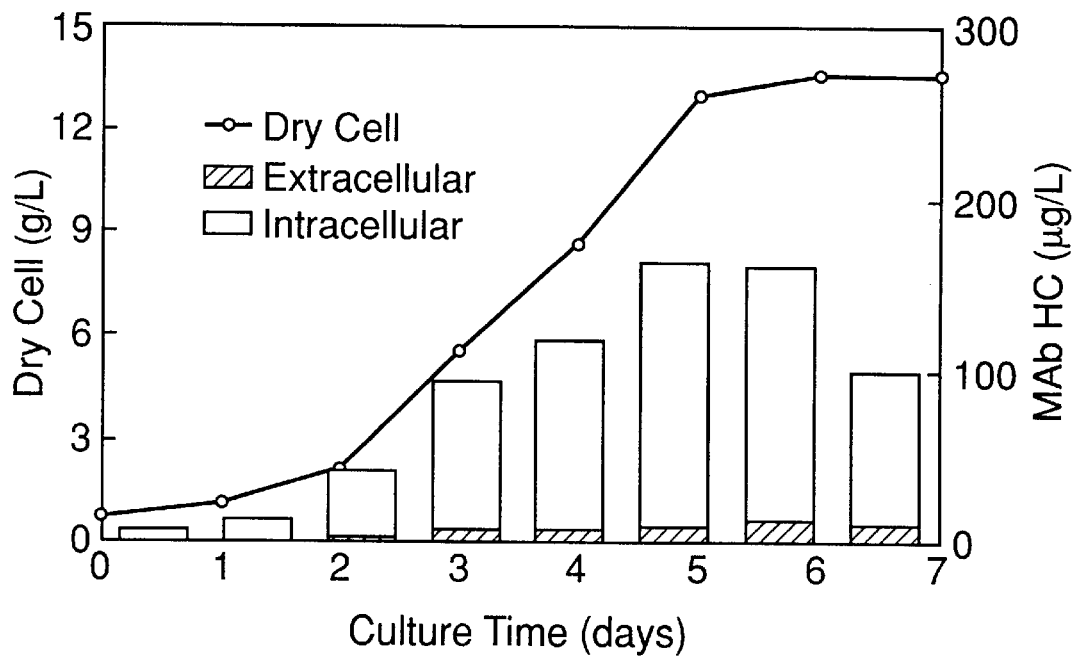
FIG. 3 shows the results of batch culture of transformed tobacco suspension cells (cell line no. 70) in a 250-ml Erlenmeyer flask. The change in dry cell mass (line with open circles) is compared to the MAb HC concentrations (fill bar, extracellular; open bar, intracellular) based on unit medium volume.

In order to determine the kinetics of MAb HC production in batch culture, tobacco cell line no. 70 was inoculated into medium as described in the Materials and Methods, above. As shown in FIG. 3, the growth of the cells was characterized by a day or sot of lag phase followed by about 3 days of exponential growth before stationary phase was reached. The production of MAb HC (μg/l medium) followed a similar trend of increasing amounts of synthesized protein except during the stationary phase when MAb HC levels began to fall. This indicates that the production of MAb HC is growth related and suggests that during the stationary phase, loss of the MAb HC is beginning to occur faster than synthesis. However, under these culture conditions, the amount of MAb HC that was secreted into the culture medium was less than 10% of the total measurable MAb HC inside the cells.

Localization of MAb HC

It has been previously reported that transgenic plants producing either the individual immunoglobulin heavy-chain variable region ($V_H$) domains (Benvenuto et al., *Plant Molecular Biology* 17:865–874, 1991) or full-length mouse antibody chains preferentially target these proteins to the plant cell plasma membrane (Hiatt et al., *Nature* 342:76–78, 1989; During et al., *Plant Mol. Biol.* 15:281–293, 1990; Hein et al., *Biotechnol. Prog.* 7:455–561, 1991; Firek et al., *Plant Molecular Biology* 23:861–870, 1993; and Ma et al., *Eur. J. Immunol.* 24:131–138, 1994). In each case, the antibody polypeptides contained a mammalian leader sequence. The plasmid pH$\gamma_1$360E from which the mouse MAb HC cDNA was obtained also encodes a native leader sequence that targets the mature antibody to an extracellular space in the animal system. In this construct the animal leader sequence was not removed in order to determine if the heterologous leader was functional in plant cells, directing the secretion of the mature antibodies from plant cells.

Even though FIG. 3 shows that a small portion of the MAb HC was found in the medium, it was not known if the MAb HC was secreted into the medium through the plasma membrane and cell wall or if its presence in the medium was the result of cell lysis. For this reason, the level of MAb HC both within the plant cell and in the culture medium was determined.

To determine the location of the synthesized MAb HC, cells were first separated from the culture medium and the MAb HC concentration in the medium measured (the extracellular fraction). To determine the intracellular localization of the MAb HC, the cells were lysed and the cytoplasmic fraction separated from the particulate fraction by centrifugation. The particulate fraction contained the cell protoplasmic membrane, cell wall and organelle fractions. Each isolated fraction was extracted using high salt as described in the Materials and Methods, above. From such a fractionation procedure of a four-day-old suspension culture (cell line no. 70), it was found that only 4% (0.5 μg/g dry weight) of the produced MAb HC was located in the medium. On the other hand, about 30% (3.8 μg/g dry weight) was found in the membrane fraction and the remaining 66% (7.5 μg/g dry weight) was found in cytoplasm. The large percentage of MAb HC detected in the membrane fraction suggested that the mammalian signal peptide was directing the MAb HC to the membrane, consistent with previous reports of expression of antibodies in plants.

Figure 4:
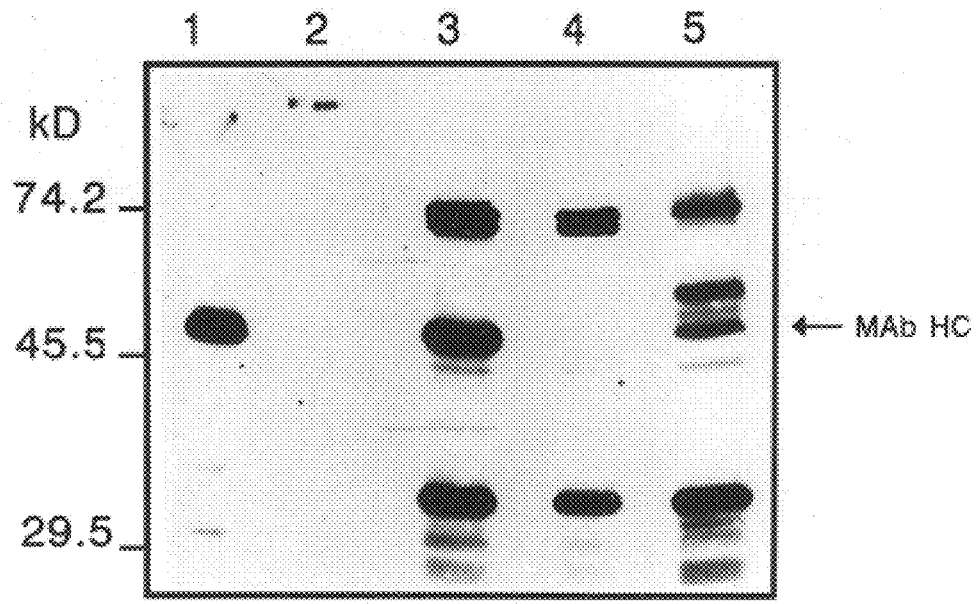
FIG. 4 shows the results of Western blot analysis of the intracellular contents of transformed cell line No. 70 for the expression of MAb HC. Lane 1, baculovirus-produced MAb HC with anti-p-azophenylarsonate specificity (100 ng). Lane 2, blank. Lane 3, control NT-1 cells spiked with 100 ng baculovirus-produced MAb HC with anti-p-azophenylarsonate specificity. Lane 4, control NT-1 cells alone. Lane 5, cell line no. 70.

FIG. 4 shows the results of Western blot analysis of the intracellular contents of cell line no. 70, affinity purified over a p-azophenylarsonate-Sepharose 4B matrix. For each cell line, 1 ml of intracellular supernatant was purified over protein G-Sepharose. As controls, intracellular contents from the parental plant cell line culture, NT-1 and 100 ng of the baculovirus-expressed p-azophenylarsonate MAb HC were also purified over the affinity matrix. The Western blot reveals at least two major proteins that are unique to cell line no. 70, the proteins having molecular masses of ~50 and ~55 kDa consistent with the expected molecular mass of the MAb HC.

Figure 5:
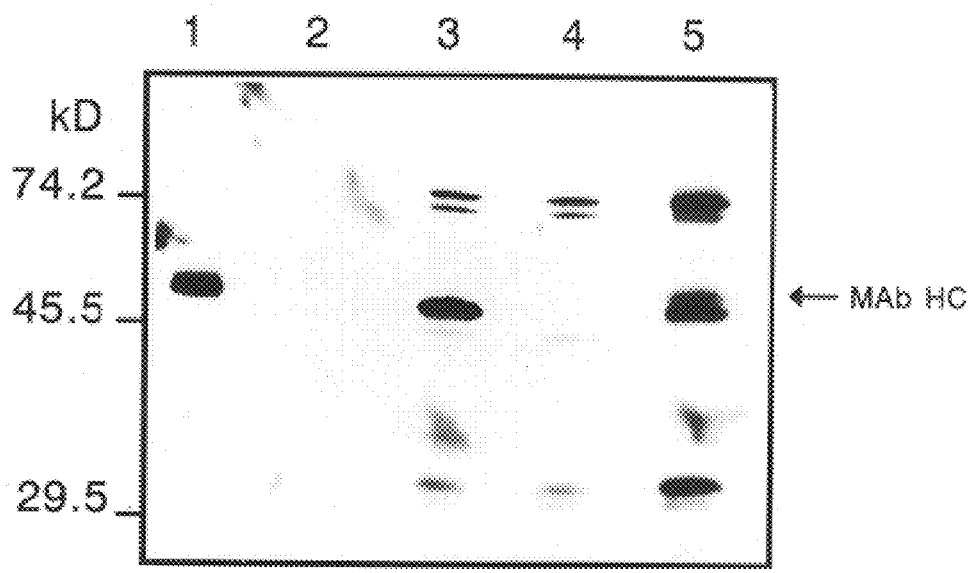
FIG. 5 shows the results of Western blot analysis of the intracellular contents of transformed cell line No. 70 for the expression of MAb HC. Lane 1, baculovirus-produced mouse Ig γ heavy chain with anti-p-azophenylarsonate specificity (100 ng). Lane 2, blank. Lane 3, control NT-1 cells spiked with 100 ng authentic mouse Ig γ heavy chain with anti-p-azophenylarsonate specificity. Lane 4, control NT-1 cells alone. Lane 5, cell line no. 70.

As antibodies produced in plants have a different glycosylation patterns than antibodies produced in animals (Hein et al., *Biotechnol. Prog.* 7:455–561, 1991), it was of interest to determine if the MAb HC produced in the clone no. 70 cell line would recognize protein G, a protein which specifically recognizes mouse IgG. In a similar experiment where the intracellular contents were affinity purified over protein G sepharose, similar results were found with two major proteins unique to cell line no. 70 with molecular masses of ~50 and 55 kDa. FIG. 5 shows the results of Western blot analysis of the intracellular contents of transformed cell line No. 70 for the expression of MAb HC comparing baculovirus-produced mouse Ig γ heavy chain with anti-p-azophenylarsonate specificity (100 ng); control NT-1 cells spiked with 100 ng authentic mouse Ig γ heavy chain with anti-p-azophenylarsonate specificity; control NT-1 cells alone; and cell line no. 70. For each cell line, 1 ml of intracellular supernatant was purified over an antigen-specific column (p-phenylarsonte-Sepharose 4B protein G-Sepharose). These results demonstrate that cell line no. 70 produced functional MAb HC.

Table 2 shows the cellular location of MAb and soluble proteins after four days of suspension culture of cell line no. 70. The intracellular fraction was divided by two general regions, cytoplasmic and membrane. The MAb HC concentration was determined by ELISA and the soluble protein level was determined by the Bradford assay (see Materials and Methods). As shown in Table 2, when comparing protein levels (mg/g DC) between the intracellular and the extracellular fractions, only 0.8% of the total protein in the culture was found in the medium. On the other hand, when comparing MAb HC (mg/g DC) levels, 4% of the total MAb HC was found in the medium. This finding suggested that the relative amount of HC MAb/total protein in the medium was five times higher relative to the MAb HC/protein ratio found inside the cell. This is indicated in the third column of Table 2. If the MAb HC was not secreted but instead leaked out of the cell, at least 4% of other cellular proteins should also have been present in the medium. These observations indicate that the tobacco cells selectively secreted the MAb HC.

TABLE 2

Cellular location of MAb and soluble proteins after 4 days of suspension culture of cell line no. 70

| Fraction | MAb HC μg/g DC | Protein mg/g DC | MAb HC μg/g DC |
|---|---|---|---|
| Cytoplasm | 7.5 | 270 | 28 |
| Membrane | 3.8 | 116 | 33 |
| Medium | 0.5 | 3.3 | 152 |

Decreasing Levels of Secreted Mab HC

Figure 6:
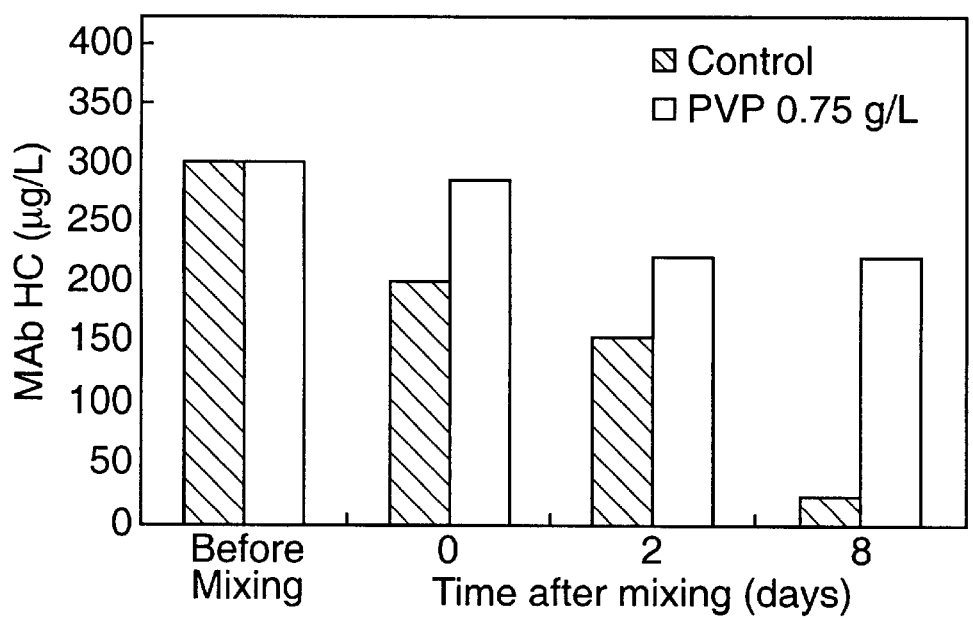
FIG. 6 shows the effects of the addition of polyvinylpyrrolidone (PVP) on the stability of baculovirus MAb HC. Control: MAb HC added to medium without PVP.

To determine whether MAb HC secreted from the cells was lost after secretion, 350 μg/l of baculovirus-expressed MAb HC (Hasemann et al., *Proc. Natl. Acad. Sci. USA* 87:3942–3946, 1990) was added to the plant cell medium. By ELISA it was determined that MAb HC added to the culture medium rapidly fell to 54% of initial values (FIG. 6). The concentration of MAb HC in the conditioned medium obtained from a six-day old culture of untransformed tobacco cells (NT-1) was similar to that of fresh medium. SDS-PAGE analysis of MAb HC was consistent with the ELISA results and showed a decrease in MAb HC concentration. No degradation products were detected, suggesting that the loss of protein was due, at least in part, to adsorption of protein to the surface of the culture vessel.

To determine if this decrease in MAb in plant cell medium could be prevented, 0.075% polyvinylpyrrolidone (PVP, mol. wt. 360,000 at 0.75 g/l) was added to cell medium spiked with 350 μg/l of baculovirus-expressed MAb HC. PVP is a versatile polymer that is water-soluble, metabolically and physiologically inert, and exhibits excellent complexing, stabilizing and colloidal properties (Anderson et al., *J. Appl. Poly. Sci.* 23:2453–2462, 1979). The incubation conditions were those used for batch suspension cultures. In the control, MAb HC was added to the medium without PVP. As shown in FIG. 6, it is clear that MAb HC concentrations could be maintained under culture conditions for at least two days by adding PVP to the medium. Concentrations of PVP up to 3.0 g/l did not adversely affect the growth of the tobacco cells in culture.

Figure 7:
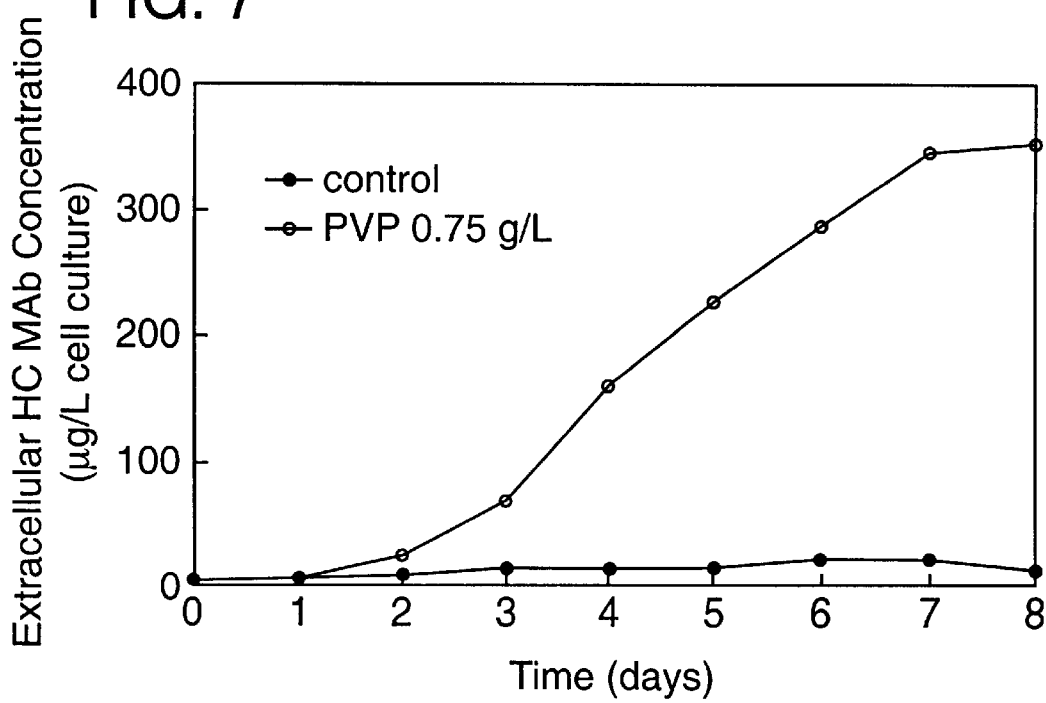
FIG. 7 shows the effects of PVP on extracellular MAb HC concentrations during eight days of culture of a batch suspension culture of cell line No. 70. Control: cultures of No. 70 grown without PVP in the culture medium.

To determine the ability of PVP to maintain the secreted MAb HC levels, clone no. 70 was grown in batch suspension culture in the presence of 0.75 g/l PVP in 250-ml Erlenmeyer flasks containing 60 ml of medium. Control cultures of No. 70 were grown without PVP in the culture medium. The results are shown in FIG. 7. During 8 days of culture, PVP increased the yield of secreted MAb HC in the culture medium 35-fold compared to the control (from 10 $\mu$g/l to 360 $\mu$g/l culture medium).

Secreted MAb HC

Figure 8:
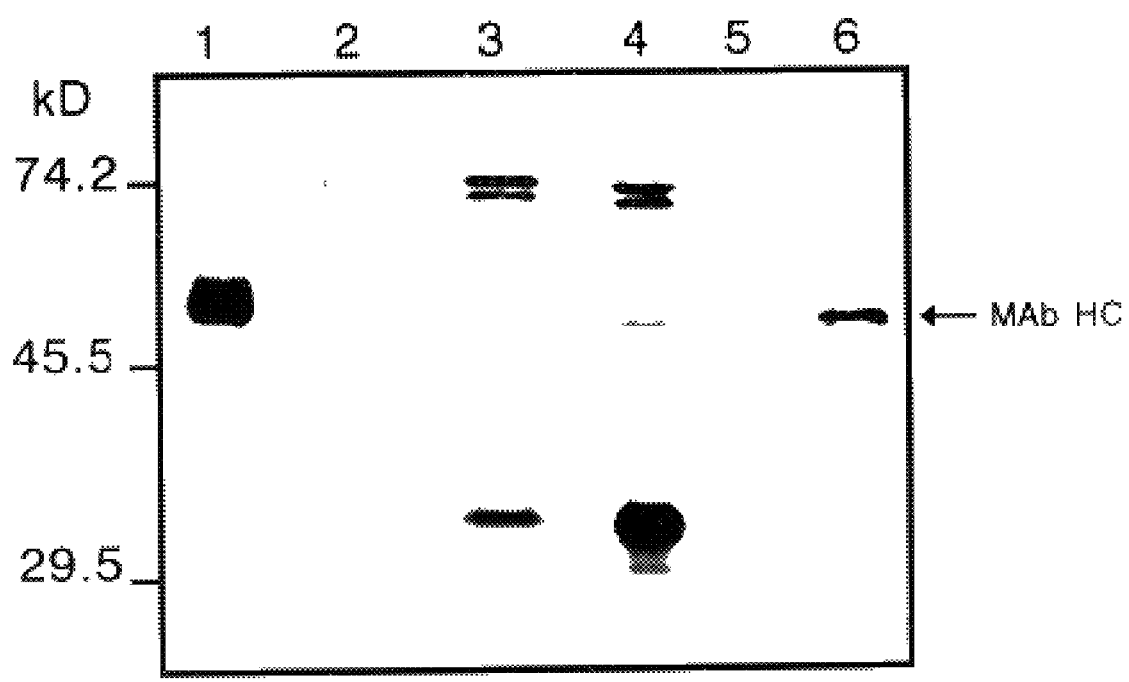
FIG. 8 shows the results of Western blot analysis of MAb HC present in total protein secreted into culture medium. Lane 1, baculovirus-produced MAb HC with anti-p-azophenylarsonate specificity (100 ng). Lane 2, blank. Lane 3, control NT-1 alone. Lane 4, control NT-1 spiked with 100 ng baculovirus-produced MAb HC with anti-p-azophenylarsonate specificity. Lane 5, blank. Lane 6, cell line No. 70.

With the finding that increased levels of MAb HC could be obtained in culture medium with the addition of a stabilizer, it was of interest to determine if the secreted protein would possess similar characteristics compared to the intracellular MAb HC and baculovirus-produced mouse Ig $\gamma$ heavy chain. Therefore, to identify the presence of a polypeptide in the medium that would be recognized with the goat anti-mouse IgG, total protein from 1.0 ml of medium was precipitated with 15% TCA, separated on 10% SDS-PAGE, and analyzed by Western blotting. The results are shown in FIG. 8. It was found that a single protein with a mass of ~50 kDa was produced by cell line no. 70 that was not produced by the control NT-1 cells. However, a smaller (~32 kDa), but prominent anti-mouse IgG cross-reacting band was also present in the precipitates from the clone 70 cells.

Figure 9:
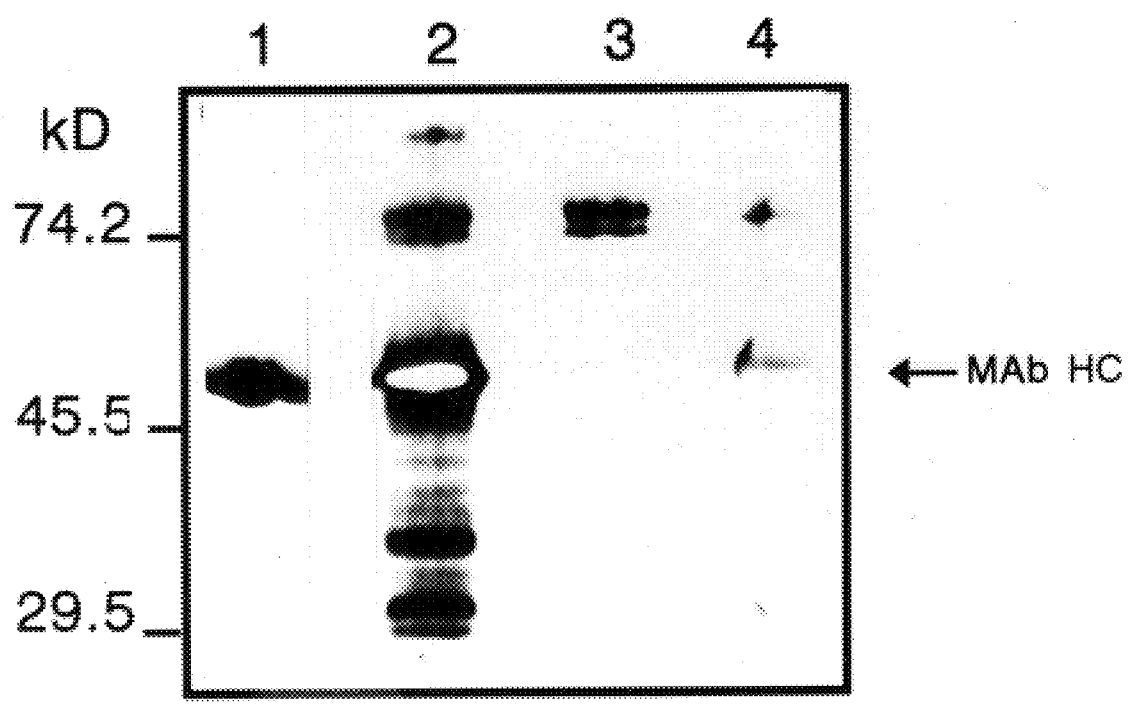
FIG. 9 shows antigen binding function as determined from a Western blot of MAb HC derived from affinity purification of culture medium on p-phenylarsonate-sepharose 4B. Lane 1, baculovirus-produced MAb HC with anti-p-azophenylarsonate specificity (100 ng). Lane 2 control NT-1 cells spiked with 100 ng baculovirus-produced MAb HC with anti-p-azophenylarsonate specificity. Lane 3, control NT-1 cells alone. Lane 4, cell line No. 70.

To verify that the anti-IgG cross reacting proteins secreted into the medium were functional, 1.0-ml aliquots of medium from a six-day-old culture of cell line no. 70 were affinity purified over either a p-azophenylarsonate-Sepharose 4B affinity matrix or a protein G Sepharose affinity matrix. FIG. 9 shows antigen binding function as determined from Western blotting of MAb HC derived from affinity purification of culture medium on the antigen specific column, p-phenylarsonate-Sepharose 4B. The results were identical for both affinity matrices in that only the ~50 kDa protein was bond by the affinity matrixes. In a separate experiment, it was verified that the 50 kDa heavy chain from the other monoclonal antibodies with unrelated specificities were not retained by the p-azophenylarsonate-Sepharose 4B affinity matrix nor was the more abundant ~32-kDa IgG cross-reacting peptide fragment from the cell line no. 70.

Discussion

Inclusion of a protein stabilizing agent such as PVP in the growth medium of tobacco plant suspension cultures dramatically enhanced recovery (greater than 35-fold) of the secreted foreign protein without adversely affecting the rapid growth characteristics of the NT-1 tobacco cell line. These results cannot be attributed to artifactual increases in cell death or breakage (Table 2). These findings support the "default pathway hypothesis" that, as in mammalian plasma cells, antibodies or other mammalian polypeptides expressed in plants would be secreted (Chrispeels, *Ann. Rev. Plant. Physiol. Plant Mol. Biol.* 42:21–53, 1991), as long as the molecular size or chemical nature of the polypeptide can be accommodated by the pore size of the plant cell wall.

These findings also further support the notion that plants can serve as an abundant source of economically important proteins (Moffat, *Science* 256:770–771, 1992). High-level production of functional foreign proteins has already been achieved in intact transgenic plants (Ma et al., *Science* 268:716–719, 1995; Hiatt et al., *Nature* 342:76–78, 1989; and Firek et al., *Plant Moiecular Biology* 23:861–870, 1993). However, the major drawback in using transgenic plants for production of large quantities of pure protein has been the cost of purifying the recombinant foreign protein away from endogenous plant proteins (Holzman, *Genetic and Engineering News* 14:1, 1994). As an alternative approach to producing foreign proteins in intact transgenic plants, secretion from single cell suspension cultures offers an advantage because the medium for growing plant suspension cultures contains only simple salts, sugars and vitamins, none of which should complicate purification (Firek et al., *Plant Molecular Biology* 23:861–870, 1993). Therefore, purification costs of expressed foreign proteins from plants would be significantly reduced if the foreign protein were to be secreted directly into the growth medium. Until now the use of plant cell suspension cultures has been limited because of the apparent low-level production and secretion into the extracellular medium of the desired protein (Sijmons et al., *Bio/Technology* 8:217–221, 1990; Ma et al., *Science* 268:716–719, 1995; Hein et al., *Biotechnol. Prog.* 7:455–561, 1991; Firek et al., *Plant Molecular Biology* 23:861–870, 1993; and Ma et al., *Eur. J. Immunol.* 24:131–138, 1994).

The nature of the leader sequence appears to play an important role in the secretion of heterologous polypeptides from plant cells into the culture medium. Proper assembly of intact recombinant nascent antibody heavy and light chains in transformed tobacco plant cells requires the native or heterologous signal peptides (Hiatt et al., *Nature* 342:76–78, 1989; Hein et al., *Biotechnol. Prog.* 7:455–561, 1991). The signal peptide is required to target the antibody for secretion into the endoplasmic reticulum and through the plasma membrane into the apoplastic space. However, even though assembled antibody molecules appear to be secreted through the plasma membrane, they apparently cannot be efficiently secreted through the cell wall into the extracellular medium. As a result, the assembled antibody accumulates in the apoplastic space (Hiatt et al., *Nature* 342:76–78, 1989; and Hein et al., *Biotechnol. Prog.* 7:455–561, 1991). An attempt to replace the native signal peptide of the murine antibody with a barley $\alpha$-amylase signal peptide led to an unexpected mistargeting of the immunoglobulin chains to the chloroplast (During et al., *Plant Mol. Biol.* 15:281–293, 1990). On the other hand, other plant signal peptides known to target proteins to the endoplasmic reticulum have been shown to be as effective as mammalian signal peptides in causing secretion into the apoplastic space (Firek et al., *Plant Molecular Biology* 23:861–870, 1993).

It is also possible that the size of the recombinant protein or protein complex also plays a role in secretion of foreign proteins through both the plasma membrane and cell wall. The assembly of immunoglobulin chains into large macromolecular complexes too large to pass through the cell wall may account for the failure of plant cells to secrete the assembled molecules into the medium (Milburn, *Water Flow in Plants,* Longmnan, London, 1979; Carpita et al., *Science* 205:1144–1147, 1979). It has been estimated that the exclusion limit of the plant cell wall is equivalent to a globular protein of approximately 20 kDa (Carpita et al., *Science* 205:1144–1147, 1979) to 29 kDa (Pluckthun, *Immunol. Rev.* 130:151–188, 1991; and Bird et al., *Science* 242:423–426, 1988). Intact immunoglobulins (ca. 150 kDa) have been reported to be secreted through the walls of cultured tobacco callus cells (Hein et al., *Biotechnol. Prog.* 7:455–461, 1991), albeit into the apoplastic space. We have found that an immunoglobulin chain with a molecular mass of ~50 kDa is capable of passing through the cell wall into the medium. Whether this 50-kDa species functions as a monomer or dimer in binding antigen (Hamers-Casterman et al., *Nature* 363:446–448, 1993) is not known. If dimers are the species being eluted on the antigen specific column, it is possible that dimer formation occurs outside the cell wall. It appears from this study that the slightly larger molecular weight species (greater than 50 kDa to ~55 kDa) detected by Western blot analysis in the intracellular contents of cell line no. 70 (FIGS. 4 and 5) was not secreted into the culture medium (FIGS. 8 and 9). Thus, the size limit for efficient secretion of foreign polypeptides from plant cells is unknown. The role played by the chemical nature of the recombinant protein in size exclusion for secretion into the culture medium is likewise unknown.

Compared to the successful production of smaller human proteins like insulin, human growth hormone and various interferons, the production of some proteins such as assembled antibodies and the large human serum albumin at useful levels has not previously been reported (Sijmons et al., *Bio/Technology* 8:217–221, 1990; and Hiatt et al., *Nature* 342:76–78, 1989). These findings demonstrate that some proteins, such as mouse IgG (FIG. 5), are lost from aqueous environments, as determined by ELISA assays. However, even at low concentration, such proteins can be maintained in solution by addition of polypeptide stabilizing agents such as PVP or gelatin to the culture medium.

A further important consideration for economic production of large quantities of clinically or therapeutically useful proteins is that the protein should be recovered in a biologically active form. The fact that the MAb HC could bind to protein G suggests that biological properties relating to the Fc portion of the molecule such as complement binding and Fc receptor binding are not lost as a consequence of being produced in plant culture. Moreover, these results demonstrate that PVP, for example, does not significantly affect the activity of the secreted foreign polypeptides, e.g., antigen binding or protein G binding.

Analogous to previous reports of a smaller cross-reactive fragment in the crude extracellular antibody fraction (Firek et al., *Plant Molecular Biology* 23:861–870, 1993), and in the intracellular antibody fraction (Hiatt et al., *Nature* 342:76–78, 1989; Ma et al., *Eur. J. Immunol.* 24:131–138, 1994; and De Neve et al., *Transgenic Research* 2:227–237, 1993), a smaller fragment (~34 kDa) that cross-reacts with anti-mouse antibody in Western blot analysis was detected in total protein preparations and in eluates from protein G matrices. A possible explanation for such proteolytic attack is improper addition of glycans (Olden et al., *Biochim. Biophys. Acta.* 650:209–232, 1982). It appears that N-linked glycans promote protein folding and transport and protect against proteolytic breakdown (Chrispeels, *Ann. Rev. Plant. Physiol. Plant Mol. Biol.* 42:21–53, 1991). It may be that the recombinant protein is not efficiently glycosylated at one specific place and as a result a portion of the molecule is clipped yielding a single smaller peptide. It has also been suggested that the proteolytic clipping observed in tobacco plant cells may be Nicotiana-specific, since the same constructs expressed in Arabidopsis do not produce the smaller fragments (De Neve et al., *Transgenic Research* 2:227–237, 1993).

Example 2

Figure 10A:
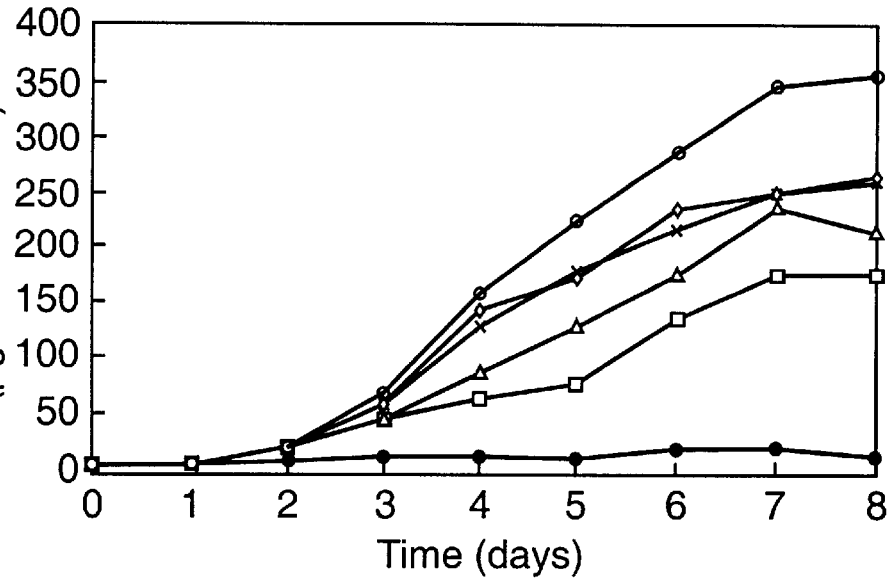
FIG. 10 shows the effect of varying concentrations of PVP on extracellular (A) and intracellular HC MAb production (B) by batch suspension cultures of NT-1 cells.
Figure 10B:
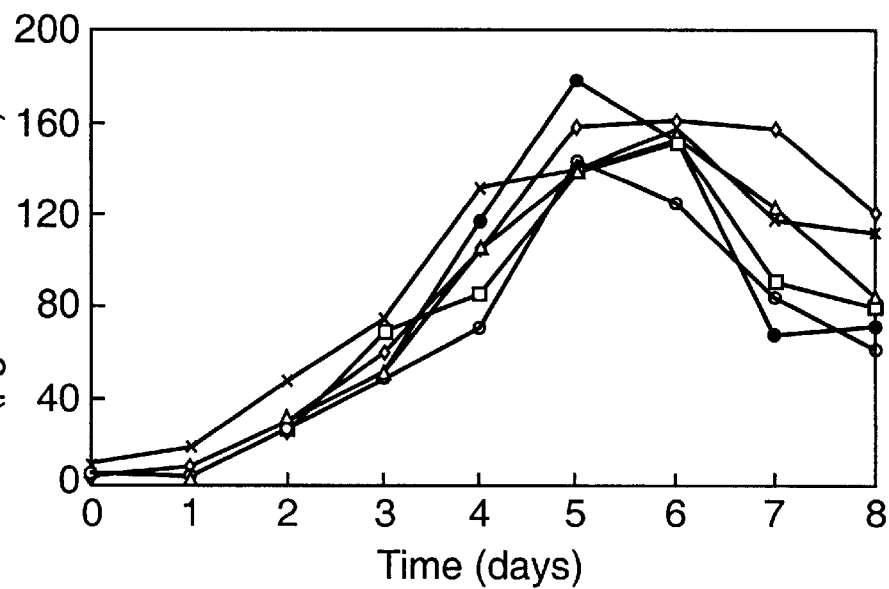

Effect of Varying Concentrations of PVP on Intracellular and Extracellular MAb HC Production In order to determine the effect of PVP at varying concentrations on the recovery of secreted proteins, MAb was produced in NT-1 suspension culture as described above. FIG. 10 shows the effect of varying concentrations of PVP (mol. wt. 360,000) in the culture medium on extracellular (top) and intracellular HC MAb production (bottom) by batch suspension cultures of NT-1 cells. At concentrations ranging from 0.25 g/l to 3.0 g/l, PVP significantly increased recovery of secreted HC MAb, with the recovery increasing with PVP concentration.

Example 3

Secretion of a Human IL-2, IL-4, and IL-10 from *Nicotiana tabacum* Cells Materials and Methods Materials and methods employed were as described above, with the following changes:

Construction of Vectors

The MAb HC cDNA cassette in plasmid pGA1132 was replaced by a similar gene cassette encoding human interleukin 2 (IL-2) (~15 kDa; Holbrook et al., *Proc. Natl. Acad. Sci. USA* 81:1634, 1984), human IL-4 (~19.5 kDa; Yokota et al., *Proc. Natl. Acad. Sci. USA* 83:5894, 1986), or human IL-10 (~18.5 kDa; Vieira et al., *Proc. Natl. Acad. Sci. USA* 88:1172, 1991).

Sampling

Calli or suspension cultures were sampled and independently weighed. 500 μl of buffer (0.1 M NaCl, 50 mM Tris, 0.25% NP-40) and 18 μl phenylmethylsulfonyl fluoride (PMSF) (0.01 g/ml) was added to 0.05 g of calli. The suspension was sonicated on ice and centrifuged at 15,000×g for five minutes. The supernatant was saved for the ELISA assay.

Results

IL-4

Figure 11:
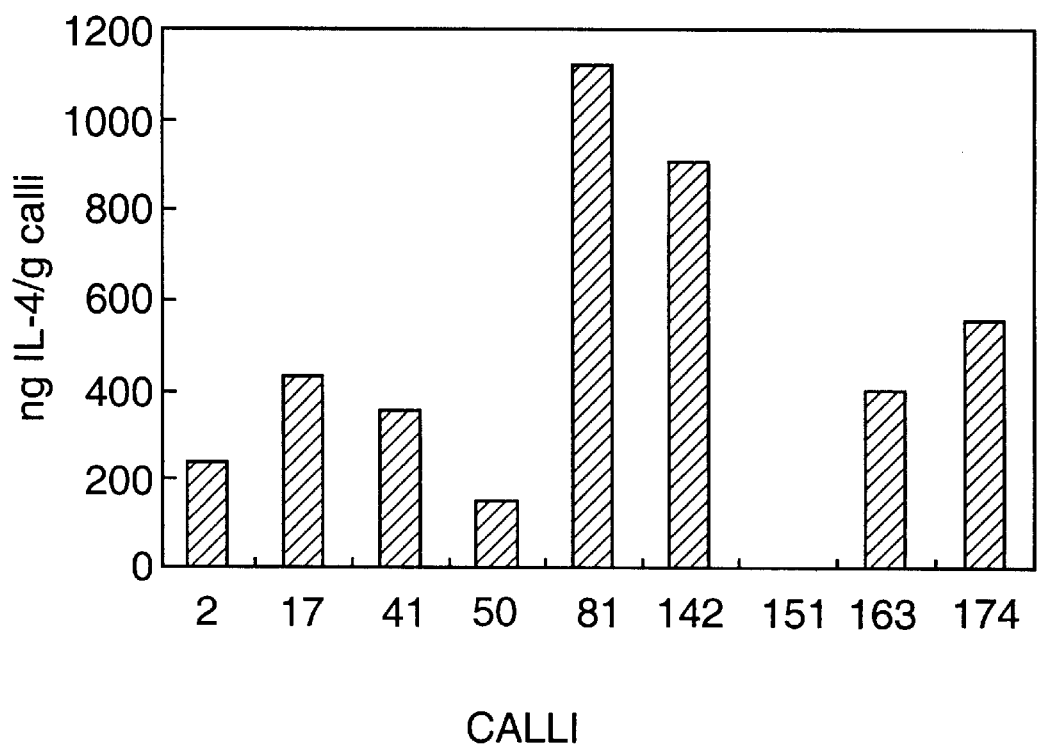
FIG. 11 shows expression of IL-4 by nine independently transformed calli as determined by ELISA (ng IL-4/g calli).

A total of 174 independent transformed calli were selected and maintained on agar medium. Ninety-nine percent of the calli were positive for IL-4 production, as determined by ELISA. Approximately 76% expressed low levels, 21% expressed intermediate levels, and 3% expressed high levels of IL-4. The average expression level was 67 ng IL-4/g calli with a high value of 178 ng/g calli. Nine cell lines have been developed into suspension cultures (2, 17, 41, 50, 81, 142, 151, 163, and 174). The expression levels for the selected calli are shown in FIG. 11.

Western blot analysis of protein in the culture medium in which the callus tissue was grown showed a band having the same size as an IL-4 positive control.

Figure 12A:
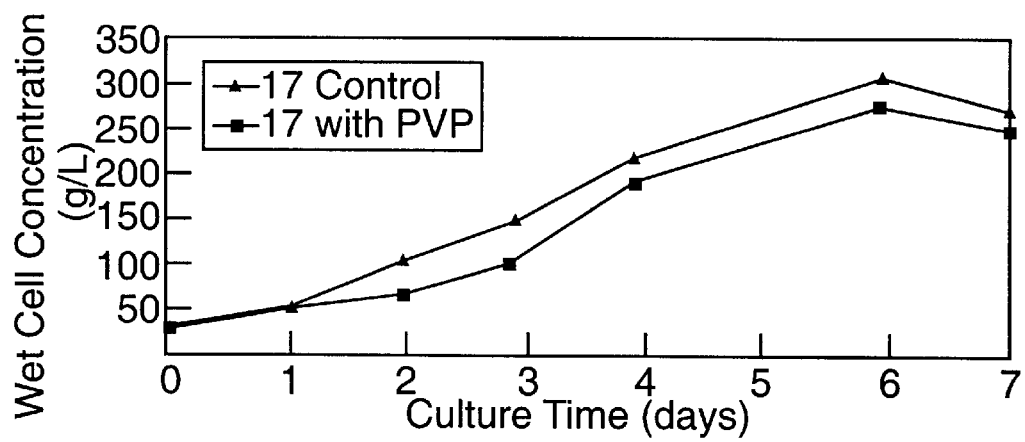
FIG. 12 shows the effect of varying concentrations of PVP on cell growth (A) and intracellular IL-4 production (B) by batch suspension cultures of clone 17.
Figure 12B:
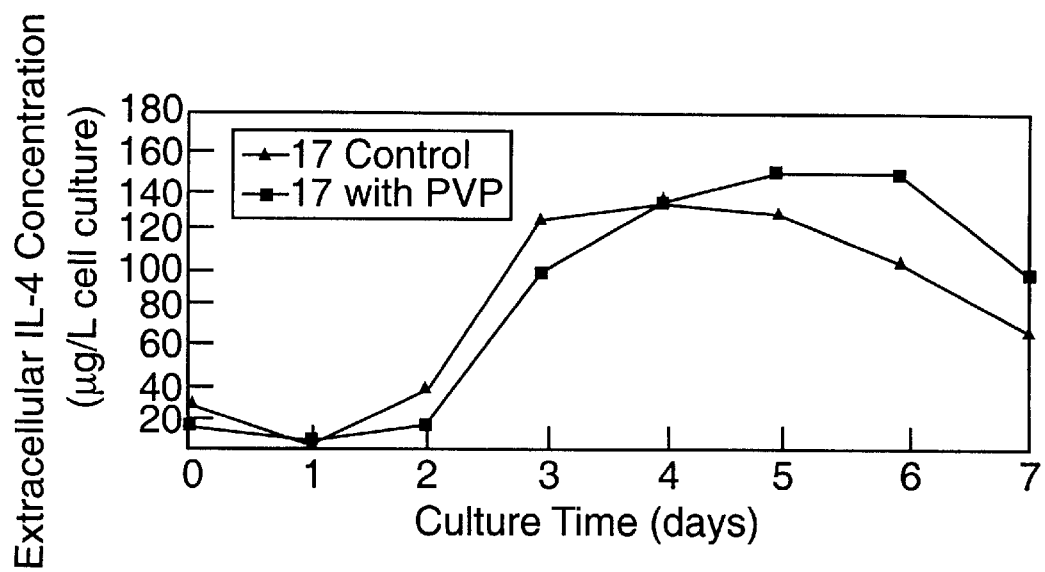

Suspension cultures expressing ILA have been examined in batch cultures both with and without PVP added to the culture medium. Samples were taken for both intracellular and extracellular production of IL-4. FIG. 12 shows the effect of PVP in the culture medium on cell growth (top) and extracellular IL-4 production (bottom) by batch suspension cultures of cell line 17. Secreted IL-4 can be recovered at high levels from culture medium lacking PVP, unlike MAb HC. The addition of PVP to the medium did not substantially affect the recovery of IL-4.

Using human recombinant IL-4 (R&D Systems, Minneapolis, Minn., cat. no. 204IL) we found that gelatin prevented a time-dependent loss of detectable IL-4, as determined by ELISA.

The concentration of IL-4 produced by the tobacco suspension cell cultures was 0.43 μg/ml culture medium, as determined by ELISA.

Western blot analysis was also performed to examine IL-4 secretion by the tobacco suspension cultures. Recombinant IL-4 produced by plant cell cultures was measured in both the medium (secreted IL-4) and in the supernatant of lysed tobacco cells. In order to examine secreted IL-4, medium (2 ml) from 6-day-old cultures was concentrated by precipitation with TCA to concentrate the protein. To examine intracellular IL-4 approximately 200 μl of the same 6-day-old cultures was centrifuged and the pelleted cells were lysed and TCA precipitated. TCA precipitates of secreted and intracellular IL-4 were washed, redissolved, then subjected to 10% SDS-PAGE and Western blot analysis using as the primary antibody a biotin-labeled rat anti-human monoclonal antibody (PharMingen) and as a secondary reagent avidin-horseradish peroxidase (Sigma). The bands were subsequently visualized by ECL (Amersham).

Figure 13:
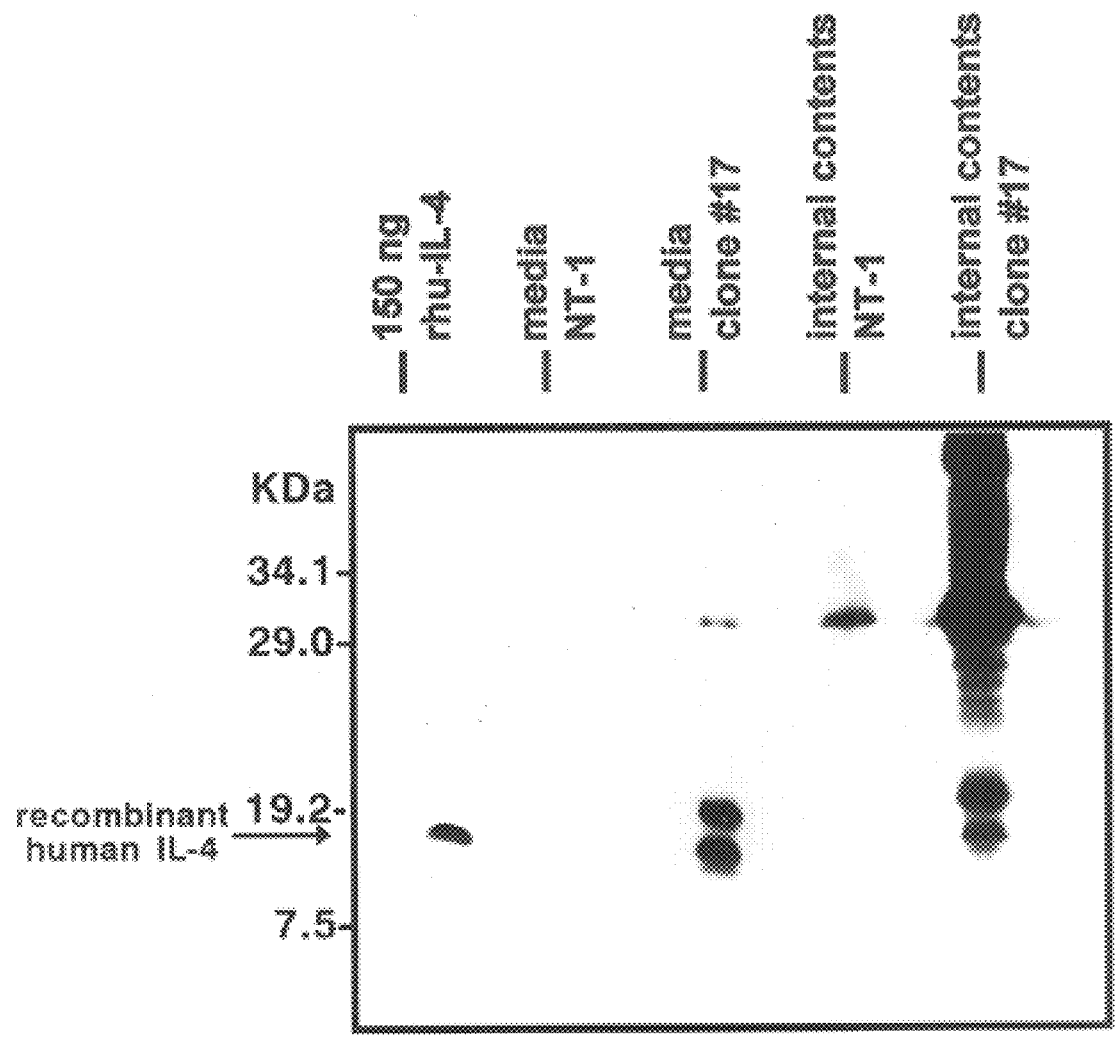
FIG. 13 shows Western blot analysis of IL-4 secreted by a suspension culture of a transformed tobacco clone. Lane 1, 150 ng recombinant human IL-4 (rhu-IL-4). Lane 2, TCA-precipitated protein from 2 ml of medium from 6-day-old cultures of NT-1 cells (negative control). Lane 3, TCA-precipitated protein from 2 ml of medium from 6-day-old cultures of suspension cultures of clone 17. Lane 4, TCA-precipitated proteins from lysates ("internal contents") of NT-1 cells pelleted from 200 µl of 6-day-old suspension cultures. Lane 5, internal contents of cells pelleted from 200 µl of 6-day-old suspension cultures of clone 17.

As shown in FIG. 13, IL-4 is secreted as two different-sized proteins that run between 18 and 22 kDa. Intracellularly, there appears to be a large amount of protein with a high molecular weight that cross-reacts with anti-IL-4 antibody. These intracellular proteins do not appear to be secreted into the medium.

Preliminary experiments have shown that high levels of IL-4 activity can be recovered from the suspension cultures. Most of the supernatants inhibit IL-4 activity at high concentrations. As the supernatants are diluted to 1/500 or 1/1000, the level of IL-4 bioactivity greatly increases, perhaps due to the low ionic strength of the plant culture medium. The biological activity of human IL-4 is assayed as described by Hu-Li et al. (*J. Immunol.* 142:800–807, 1989), using the CT.4S cell line. In order to assess IL-4 biological activity, polypeptide stabilizing agents may be omitted from the plant culture medium in order to reduce possible inhibitory activity on the CT.4S cells.

IL-10

171 independently transformed calli were selected and maintained on agar medium. Eleven percent of the calli were positive for IL-10 production, as determined by ELISA. The average expression level was 10.6 ng IL-10/g calli with a high value of 16.3 ng IL-10/g calli. Five cell lines have been developed into suspension cultures.

IL-10 was produced at levels of approximately 0.4 to 0.5 μg/ml in transformed tobacco suspension cultures as determined by ELISA.

IL-2

Eleven independently transformed calli were selected and maintained on agar medium. Eighty-two percent of the calli were positive for IL-2 production, as determined by ELISA (Collaborative Research). The average expression level was 140 ng IL-2/g calli with a high value of 366 ng IL-2/g calli. Eight cell lines have been developed into suspension cultures.

Figure 14:
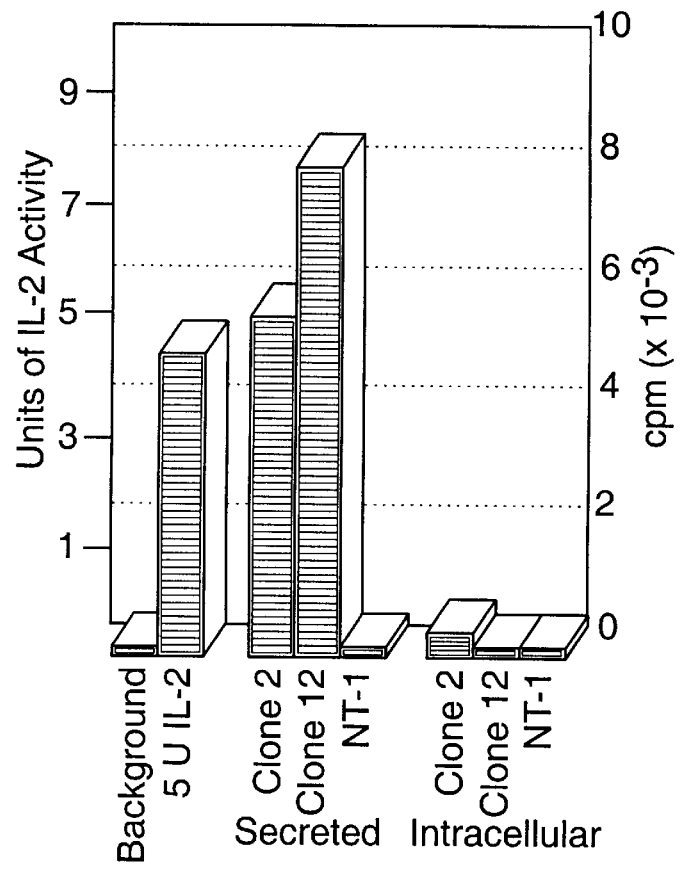
FIG. 14 shows the activity of recombinant IL-2 secreted into the medium by suspension cultures of transformed tobacco clones 2 and 12.

In order to assay for IL-2 activity, we employed an IL-2 biological assay system using the IL-2-dependent murine cell line CTLL-2, in which IL-2 activity is based on the level of incorporation of $^3$H-thymidine into cellular DNA and compared to a standard curve of recombinant IL-2 run at the same time as the samples (Gillis et al., *J. immunol.* 129:2027–2032, 1978). In 96-well microliter plates, $5 \times 10^3$ IL-2dependent CTLL-2 cells that had been deprived of IL-2 for two days were suspended to a final total volume of 200 μl. Fifty-μl samples of culture medium or of cell lysates made from pelleted suspension cultures of plant cells of clone 2 and clone 12 were diluted to the original volume of culture medium and tested in a 28-hour proliferation assay. In the assay, the CTLL-2 cells were exposed to sample for 20 hours, then pulsed with $^3$H-thymidine for an additional 8 hours. FIG. 14 clearly demonstrates secretion of IL-2 by clones 2 and 12.

Because PVP is somewhat inhibitory, we cultured IL-2-expressing NT-1 suspension culture cells without a protein stabilizer for testing biological activity. In 96-well microtiter plates, $5 \times 10^3$ IL-2-dependent CILL-2 cells that had been deprived of IL-2 for two days were suspended to a final total volume of 200 μl. 50 μl samples of culture medium used to grow the grow the cells was added to a well containing 5 units (U) recombinant IL-2 standard and compared to background, the IL-2 standard alone (positive control), media collected from a 6-day-old culture of NT-1 cells (negative control) and media collected from a 6-day-old culture of the IL-2 secreting cell line, clone 2. Activity was measured in the standard proliferation assay.

Figure 15:
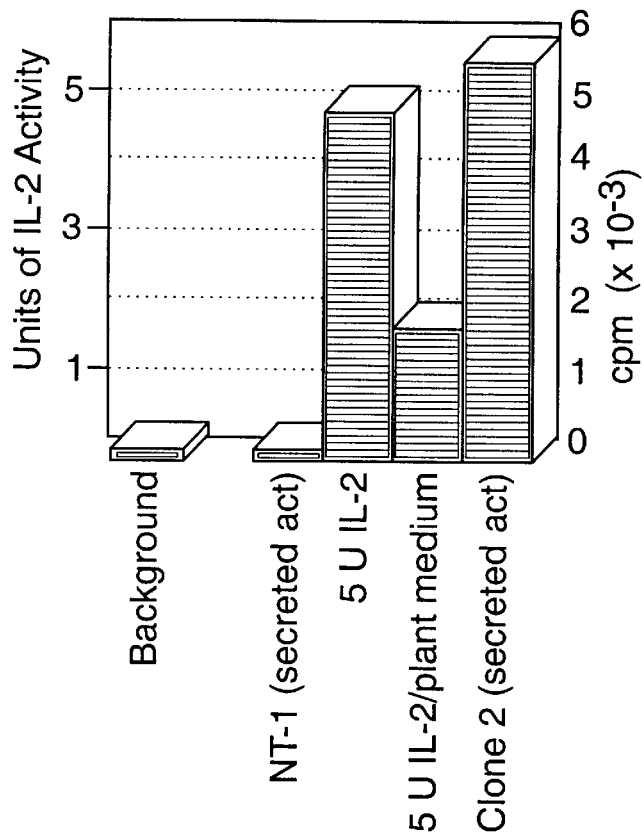
FIG. 15 shows the effect of plant cell culture media on the IL-2 activity of medium collected from a 6-day-old suspension culture of transformed tobacco clone 2.

The inhibitory activity of the medium alone appears to be due to the change in osmolarity induced by the plant cell medium. Large volumes of MS medium effectively lowers the osmolarity of the medium required by the assay cells for optimal growth. Therefore, the actual IL-2 activity is thought to be substantially higher than that observed. Nevertheless, as shown in FIG. 15, IL-2 was clearly secreted into the medium. Without a protein stabilizer, IL-2 was present at approximately 0.15 μg/ml. To confirm levels of IL-2 expression, one can perform Western blotting using anti-IL-2 antibodies (Immunotech).

These experiments indicate that various interleukins are also secreted by and can be recovered from plant cell suspension cultures. In each case, secretion was directed by the mammalian signal peptide at the N-terminal end of each of the interleukin polypeptides.

Example 4

Secretion of Human GM-CSF from *Nicotiana tabacum* Cells

Figure 17:
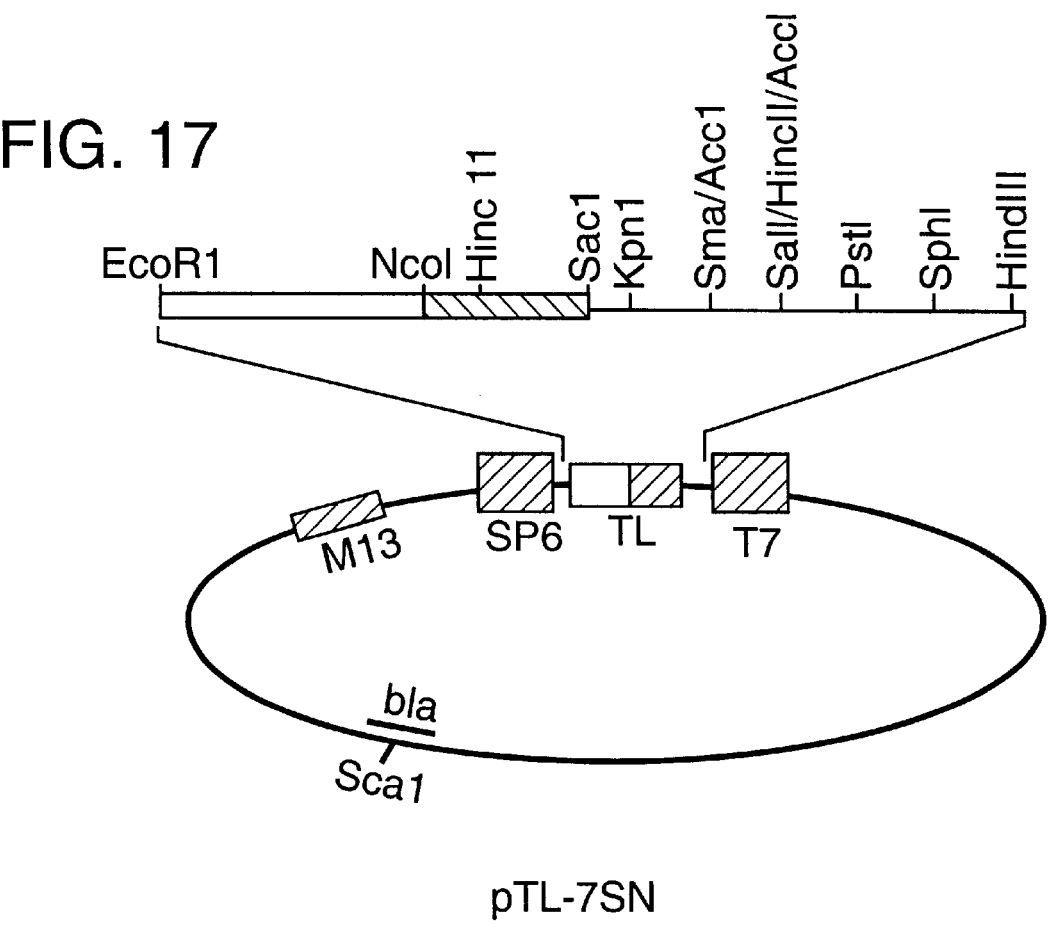
FIG. 17 shows a vector for expression of a human granulocyte-monocyte colony stimulating factor (GM-CSF) transgene in plant cells that includes: SP6 and T7 promoters flanking a tobacco etch viral (TEV) 5'-leader sequence (lacking the first 12 nucleotides); a polylinker sequence for insertion of a sequence coding for GM-CSF; a promoter for replication of the vector in bacterial cells (shown is the M13 phage promoter); and a selectable marker (shown is bla).

In experiments similar to those discussed above, *N. tabacum* NT-1 cells are transformed with a GM-CSF coding sequence (see Kanakura et al., *Blood* 77:1033–1043, 1991) inserted into the polylinker of pTL-7SN (FIG. 17) so as to be expressed in the plant cells. This construct includes the tobacco etch viral (TEV) 5' leader sequence (Gallie et al., *Gene* 165:233–238, 1995) lacking the first 12 nucleotides. GM-CSF protein levels are assayed by ELISA (R&D Systems, Minneapolis, Minn., cat. no. DGM00). GM-CSF biological activity is assayed as described in *Current Protocols in Immunology*, Coligan et al., eds., supplement 18, pp. 6.4.6–6.4.8, 1996.

All publications or patent applications cited herein are incorporated herein by reference to the same extent as if each individual publication or patent application was specifically and individually indicated to be incorporated by reference.

This invention has been detailed both by example and by direct description. It should be apparent that one having ordinary skill in the relevant art would be able to surmise equivalents to the invention as described but which would be within the spirit of the foregoing description. Those equivalents are to be included within the scope of this invention.

What is claimed is:

1. A method of producing a polypeptide in plant cell culture comprising the steps of:

providing an aqueous plant culture medium comprising a polypeptide stabilizing agent;

providing a plant cell transformed with an expressible transgene comprising a promoter operably linked to a polypeptide-coding sequence that encodes a polypeptide and a signal peptide that directs secretion of the polypeptide;

culturing the plant cell in the plant culture medium for a time sufficient for the polypeptide to be secreted into the culture medium, thereby producing a secreted polypeptide; and recovering the secreted polypeptide from the plant culture medium.

2. The method of claim 1 wherein the polypeptide is a mammalian polypeptide.

3. The method of claim 2 wherein the polypeptide is selected from the group consisting of immunoglobulin, cytokines, hormones, growth factors, blood clotting factors, complement components, fibrinolytic polypeptides, polymerases, and enzymes that metabolize lipids, amino acids, sugars, nucleic acids, and polysaccharides.

4. The method of claim 3 wherein the polypeptide is an immunoglobulin polypeptide.

5. The method of claim 3 wherein the polypeptide is an interleukin.

6. The method of claim 3 wherein the polypeptide is granulocyte-monocyte colony stimulating factor.

7. The method of claim 1 wherein the signal peptide is a mammalian signal peptide.

8. The method of claim 7 wherein the signal peptide is an immunoglobulin signal peptide.

9. The method of claim 8 wherein the signal peptide is a γ heavy chain signal peptide.

10. The method of claim 1 wherein the plant cell is a plant suspension culture cell.

11. The method of claim 1 wherein the aqueous medium comprises an amount of the polypeptide stabilizing agent that is effective to increase recovery of the secreted polypeptide by at least 20 percent as compared with a control aqueous plant culture medium lacking the polypeptide stabilizing agent.

12. The method of claim 1 wherein the polypeptide stabilizing agent is selected from the group consisting of polyvinylpyrrolidone, carbohydrates, alcohols, and proteins.

13. The method of claim 1 wherein the polypeptide stabilizer is polyvinylpyrrolidone or gelatin.

14. The method of claim 1 wherein the transgene further comprises a sequence selected from the group consisting of a potyvirus 5'-leader sequence and a nuclear scaffold attachment region sequence.

15. The method of claim 14 wherein the potyvirus 5'-leader sequence is a tobacco etch virus 5'-leader sequence.

16. The method of claim 14 wherein the nuclear scaffold attachment region sequence is a tobacco nuclear scaffold attachment region sequence.

17. A method of producing a mammalian polypeptide comprising the steps of:

providing an aqueous plant culture medium comprising a polypeptide stabilizing agent;

providing a plant cell transformed with an expressible transgene comprising a promoter operably linked to a polypeptide-coding sequence that encodes a mammalian polypeptide and a signal peptide that directs secretion of the polypeptide;

culturing the plant cell in the plant culture medium for a time sufficient for the plant cell to secrete the polypeptide into the culture medium, thereby producing a secreted polypeptide; and recovering the secreted polypeptide from the plant culture medium, wherein the plant culture medium comprises an amount of the polypeptide stabilizing agent that is effective to increase recovery of a secreted polypeptide by at least 20 percent as compared with a control aqueous plant culture medium lacking the polypeptide stabilizing agent.

18. A plant cell culture medium comprising an amount of a polypeptide stabilizing agent that is effective to increase recovery of a secreted polypeptide by at least 20 percent as compared with a control aqueous plant culture medium lacking the polypeptide stabilizing agent.

19. The plant cell culture medium of claim 18 wherein the polypeptide stabilizing agent is selected from the group consisting of polyvinylpyrrolidone, carbohydrates, alcohols, and proteins.

20. The method of claim 19 wherein the polypeptide stabilizer is polyvinylpyrrolidone or gelatin.

21. A DNA construct for secretion of a polypeptide from a plant cell, the DNA construct comprising:

a promoter functional in a plant cell;

a polypeptide-coding sequence, operably linked to the promoter, that encodes a polypeptide and a signal sequence that directs secretion of the polypeptide through the plasma membrane and cell wall of a plant cell; and a sequence selected from the group consisting of a potyvirus 5'-leader sequence and a nuclear scaffold attachment region sequence.

22. The DNA construct of claim 21 wherein the heterologous polypeptide is a mammalian polypeptide.

23. The DNA construct of claim 22 wherein the polypeptide is selected from the group consisting of immunoglobulins, cytokines, hormones, growth factors, blood clotting factors, complement components, fibrinolytic polypeptides, polymerases, and enzymes that metabolize lipids, amino acids, sugars, nucleic acids, and polysaccharides.

24. The DNA construct of claim 23 wherein the polypeptide is an immunoglobulin.

25. The DNA construct of claim 23 wherein the polypeptide is an interleukin.

26. The DNA construct of claim 23 wherein the polypeptide is granulocyte-monocyte colony stimulating factor.

27. The DNA construct of claim 21 wherein the signal peptide is a mammalian signal peptide.

28. The DNA construct of claim 27 wherein the signal peptide is an immunoglobulin signal peptide.

29. The DNA construct of claim 28 wherein the signal peptide is a heavy chain signal peptide.

30. The DNA construct of claim 25 wherein the signal peptide is a γ heavy chain signal peptide.

31. The DNA construct of claim 21 wherein the potyvirus 5'-leader sequence is a tobacco etch virus 5'-leader sequence.

32. The DNA construct of claim 21 wherein the nuclear scaffold attachment region sequence is a tobacco nuclear scaffold attachment region sequence.

33. The DNA construct of claim 21 wherein the transgene comprises both a potyvirus 5'-leader sequence and a nuclear scaffold attachment region sequence.

* * * * *

UNITED STATES PATENT AND TRADEMARK OFFICE
CERTIFICATE OF CORRECTION

PATENT NO. : 6,020,169
DATED : February 1, 2000
INVENTOR(S) : LEE ET AL.

Page 1 of 1

It is certified that error appears in the above-identified patent and that said Letters Patent is hereby corrected as shown below:

<u>On the Cover, [56] References Cited, Other Publications</u>:

The following reference should be added:

--Wahl et al., "Effects of Dimethyl Sulfoxide on Heavy Chain Monoclonal Antibody Production from Plant Cell Culture," *Biotech Letters* 17:463-468 (1995).--

<u>In the Specification</u>:

Column 13, line 8, "resspended" should be --resuspended--.

<u>In the Claims</u>:

Column 24, line 43, claim 24, "immunoglobulin" should be -- immunoglobulin polypeptide--.

Signed and Sealed this

Fifth Day of June, 2001

*Attest:*

*Attesting Officer*

NICHOLAS P. GODICI
*Acting Director of the United States Patent and Trademark Office*